(12) United States Patent
Gordon et al.

(10) Patent No.: US 7,087,203 B2
(45) Date of Patent: Aug. 8, 2006

(54) METHODS AND APPARATUS FOR BLOOD TYPING WITH OPTICAL BIO-DISC

(75) Inventors: John Francis Gordon, Irvine, CA (US); Susan Newcomb Hurt, Lake Forest, CA (US); David Samuel Cohen, Alphretta, GA (US)

(73) Assignees: Nagaoka & Co., Ltd., Hyogo (JP); Burnstein Technologies, Inc., Irvine, CA (US)

( * ) Notice: Subject to any disclaimer, the term of this patent is extended or adjusted under 35 U.S.C. 154(b) by 0 days.

(21) Appl. No.: 09/988,850

(22) Filed: Nov. 19, 2001

(65) Prior Publication Data

US 2002/0098528 A1 Jul. 25, 2002

Related U.S. Application Data

(60) Provisional application No. 60/252,726, filed on Nov. 22, 2000, provisional application No. 60/249,477, filed on Nov. 17, 2000.

(51) Int. Cl.
*C12M 1/34* (2006.01)

(52) U.S. Cl. .................. 422/72; 422/68.1; 422/102; 436/45; 435/4; 435/283.1; 435/287.1

(58) Field of Classification Search ............ 369/275.1, 369/275.3, 280, 282; 435/287, 6, 283, 4–7.9, 435/24, 27; 422/72, 8.1, 102, 68.1, 45; 436/45; 356/73, 437
See application file for complete search history.

(56) References Cited

U.S. PATENT DOCUMENTS

| | | | |
|---|---|---|---|
| 3,798,459 A | | 3/1974 | Anderson et al. |
| 3,799,742 A | * | 3/1974 | Coleman .................... 422/61 |
| 3,890,101 A | | 6/1975 | Tiffany et al. |
| 3,901,658 A | | 8/1975 | Burtis et al. |
| 3,979,509 A | | 9/1976 | Giaever |
| 4,284,602 A | | 8/1981 | Kelton et al. |
| 4,469,793 A | | 9/1984 | Guigan |
| 4,515,889 A | * | 5/1985 | Klose et al. .................. 435/4 |
| 4,608,344 A | | 8/1986 | Carter et al. |
| 4,650,662 A | | 3/1987 | Goldfinger et al. |
| 4,683,120 A | | 7/1987 | Meserol et al. |
| 4,847,205 A | | 7/1989 | Burtis et al. |
| 4,877,745 A | | 10/1989 | Hayes et al. |
| 4,917,865 A | | 4/1990 | Romanauskas |
| 5,061,381 A | * | 10/1991 | Burd .......................... 210/789 |
| 5,122,284 A | | 6/1992 | Braynin et al. |

(Continued)

FOREIGN PATENT DOCUMENTS

EP      0 297 394 A2    1/1989

(Continued)

OTHER PUBLICATIONS

Amigo, L; Covarrubias, Carmen; Nervi, F, Rapid isolation of vesicular and micellar carriers of biliary lipids by ultracentrifucation, 1990, vol. 31, p.341-347.*

(Continued)

*Primary Examiner*—Long V. Le
*Assistant Examiner*—Nelson Yang
(74) *Attorney, Agent, or Firm*—Knobbe, Martens, Olson & Bear, LLP

(57) ABSTRACT

This invention relates to clinical diagnostic assays and related optical bio-discs and a disc-reading apparatus. The invention is directed to a method for determining the blood cell type of an individual.

19 Claims, 24 Drawing Sheets

U.S. PATENT DOCUMENTS

| | | | |
|---|---|---|---|
| 5,160,702 A | 11/1992 | Kopf-Sill et al. | |
| 5,173,193 A | 12/1992 | Schembri | |
| 5,173,262 A | 12/1992 | Burtis et al. | |
| 5,186,844 A | 2/1993 | Burd et al. | |
| 5,191,068 A | 3/1993 | Thomson et al. | |
| 5,242,606 A | 9/1993 | Braynin et al. | |
| 5,256,376 A | 10/1993 | Callan et al. | |
| 5,281,540 A | 1/1994 | Merkh et al. | |
| 5,310,523 A | 5/1994 | Smethers et al. | |
| 5,384,261 A | 1/1995 | Winkler et al. | |
| 5,407,554 A | 4/1995 | Saurer | |
| 5,409,665 A | 4/1995 | Burd | |
| 5,413,939 A | 5/1995 | Gustafson et al. | |
| 5,457,582 A | 10/1995 | Victora et al. | |
| 5,462,839 A | 10/1995 | de Rooij et al. | |
| 5,472,603 A | 12/1995 | Schembri | |
| 5,486,335 A | 1/1996 | Wilding et al. | |
| 5,510,270 A | 4/1996 | Fodor et al. | |
| 5,518,930 A * | 5/1996 | Burd | 436/45 |
| 5,552,064 A | 9/1996 | Chachowski et al. | |
| 5,585,069 A | 12/1996 | Zanzucchi et al. | |
| 5,591,643 A | 1/1997 | Schembri | |
| 5,627,041 A | 5/1997 | Shartle | |
| 5,631,166 A * | 5/1997 | Jewell | 436/45 |
| 5,637,469 A | 6/1997 | Wilding et al. | |
| 5,750,074 A * | 5/1998 | Katzman et al. | 422/102 |
| 5,783,446 A | 7/1998 | Saul et al. | |
| 5,807,522 A | 9/1998 | Brown et al. | |
| 5,837,832 A | 11/1998 | Chee et al. | |
| 5,882,903 A | 3/1999 | Andrevski et al. | |
| 5,892,577 A * | 4/1999 | Gordon | 356/73 |
| 5,900,481 A | 5/1999 | Lough et al. | |
| 5,922,591 A * | 7/1999 | Anderson et al. | 435/287.2 |
| 5,932,799 A | 8/1999 | Moles | |
| 6,002,474 A | 12/1999 | Thomas et al. | |
| 6,013,513 A | 1/2000 | Reber et al. | |
| 6,024,883 A | 2/2000 | Jewell | |
| 6,030,581 A * | 2/2000 | Virtanen | 422/68.1 |
| 6,063,589 A * | 5/2000 | Kellogg et al. | 435/24 |
| 6,110,748 A | 8/2000 | Reber et al. | |
| 6,121,048 A | 9/2000 | Zaffaroni et al. | |
| 6,126,765 A | 10/2000 | Ohman | |
| 6,140,135 A | 10/2000 | Landegren et al. | |
| 6,143,247 A | 11/2000 | Sheppard, Jr. et al. | |
| 6,143,248 A | 11/2000 | Kellogg et al. | |
| 6,143,510 A * | 11/2000 | Hoshino et al. | 435/7.94 |
| 6,167,910 B1 * | 1/2001 | Chow | 137/827 |
| 6,176,962 B1 | 1/2001 | Soane et al. | |
| 6,221,315 B1 | 4/2001 | Giesler et al. | |
| 6,287,517 B1 | 9/2001 | Ackley et al. | |
| 6,302,134 B1 | 10/2001 | Kellogg et al. | |
| 6,319,468 B1 * | 11/2001 | Sheppard, Jr. et al. | 422/63 |
| 6,327,031 B1 | 12/2001 | Gordon | |
| 6,399,361 B1 * | 6/2002 | Brotherston et al. | 435/283.1 |
| 6,582,662 B1 * | 6/2003 | Kellogg et al. | 422/72 |
| 6,632,399 B1 | 10/2003 | Kellogg et al. | |
| 2001/0001060 A1 * | 5/2001 | Kellogg et al. | 435/7.1 |
| 2001/0055812 A1 * | 12/2001 | Mian et al. | 436/45 |
| 2002/0047003 A1 | 4/2002 | Bedingham et al. | |
| 2002/0071362 A1 | 6/2002 | Worthington | |
| 2002/0076354 A1 | 6/2002 | Cohen | |
| 2002/0098528 A1 | 7/2002 | Gordon et al. | |
| 2002/0106786 A1 | 8/2002 | Carvalho et al. | |
| 2002/0145960 A1 | 10/2002 | Worthington et al. | |
| 2002/0163642 A1 * | 11/2002 | Zoval et al. | 356/437 |
| 2002/0171838 A1 | 11/2002 | Pal et al. | |
| 2002/0172980 A1 | 11/2002 | Phan et al. | |
| 2002/0196435 A1 | 12/2002 | Cohen et al. | |
| 2003/0003464 A1 | 2/2003 | Phan et al. | |
| 2003/0054376 A1 | 3/2003 | Mullis et al. | |
| 2003/0064507 A1 | 4/2003 | Gallagher et al. | |
| 2003/0104486 A1 * | 6/2003 | Selvan | 435/7.2 |

FOREIGN PATENT DOCUMENTS

| | | |
|---|---|---|
| EP | 0 417 305 A1 | 3/1991 |
| EP | 0 521 421 A2 | 1/1993 |
| EP | 0 693 560 A2 | 1/1996 |
| WO | WO 96/04547 | 2/1996 |
| WO | WO 96/32841 | 10/1996 |
| WO | WO 97/21090 | 6/1997 |
| WO | WO 98/38510 | 9/1998 |
| WO | WO 00/05582 | 2/2000 |
| WO | WO 01/02737 | 1/2001 |
| WO | WO 01/46465 | 6/2001 |
| WO | WO 01/47638 | 7/2001 |
| WO | WO 01/87486 | 11/2001 |
| WO | WO 01/87487 | 11/2001 |
| WO | WO 02/42498 | 5/2002 |

OTHER PUBLICATIONS

Schembri et al. "Centrifugation and cappilarity integrated into a multiple analyte whole blood analysen," *Journal of Automatic Chemistry*, 17(3):99-104 (1995).

Duffy et al. "Microfabricated Centrifugal Microfluidic Systems: Characterization and Multiple Enzymatic Assays," *Anal. Chem*, 71:4669-4678 (1999).

US 6,200,755, 03/2001, Virtanen (withdrawn)

* cited by examiner

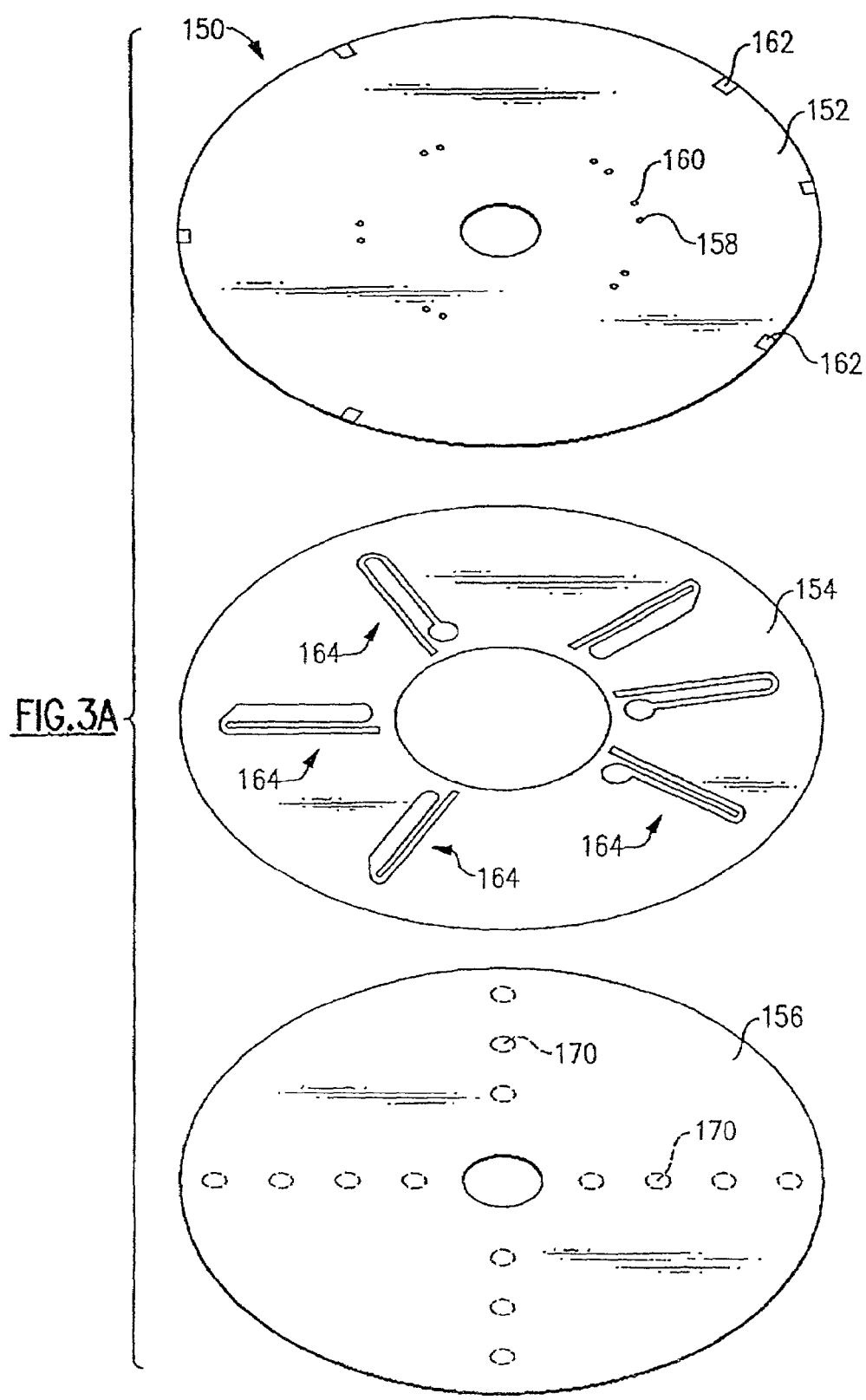

CELL CAPTURE ZONES MAY NOT UTILIZE
STREPTAVIDIN/BIOTIN
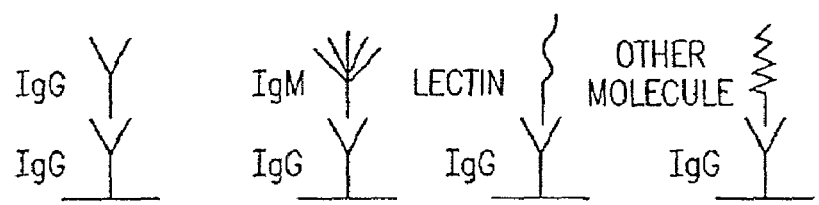
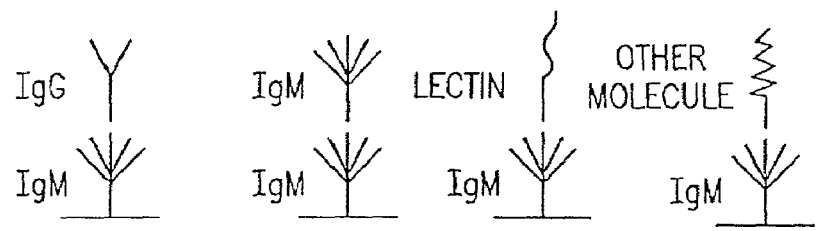
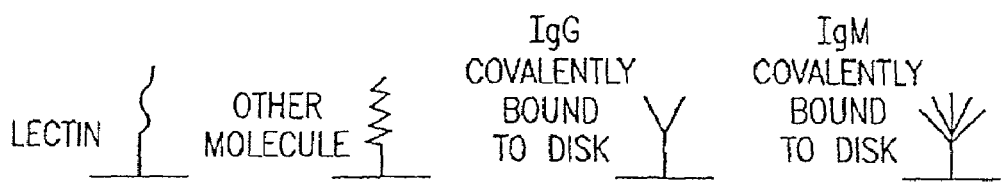
OR ANY OTHER COMBINATION
FIG.5

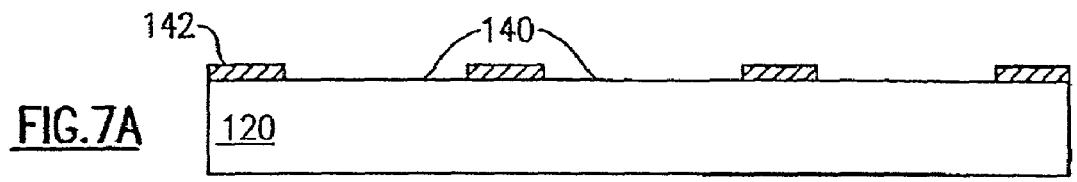
FIG. 7A
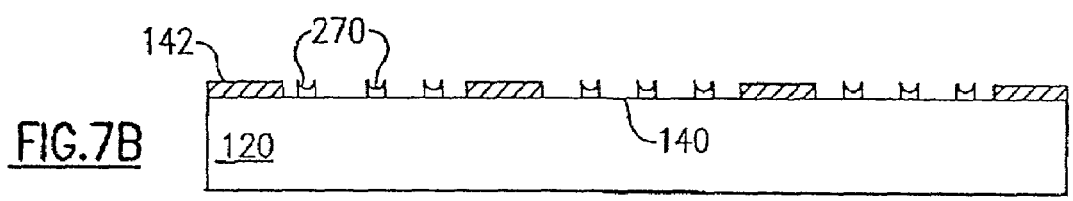
FIG. 7B
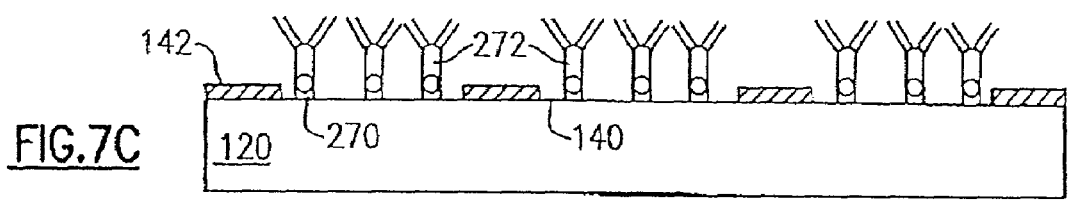
FIG. 7C
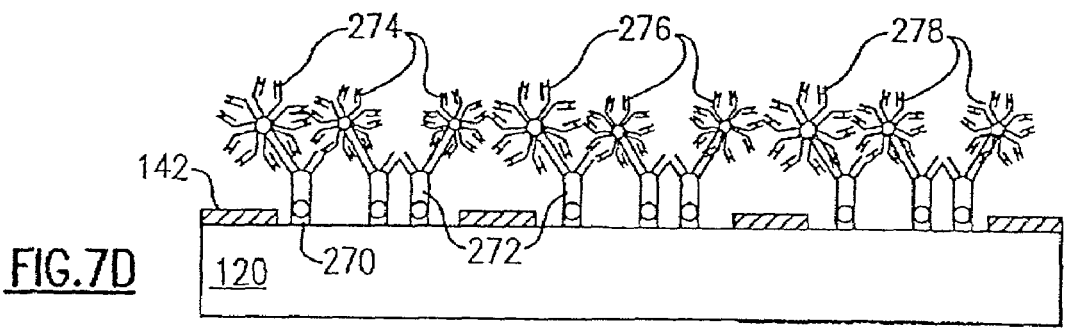
FIG. 7D
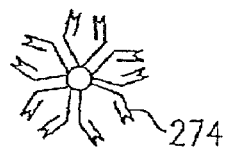
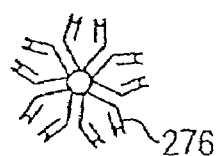
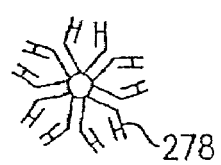

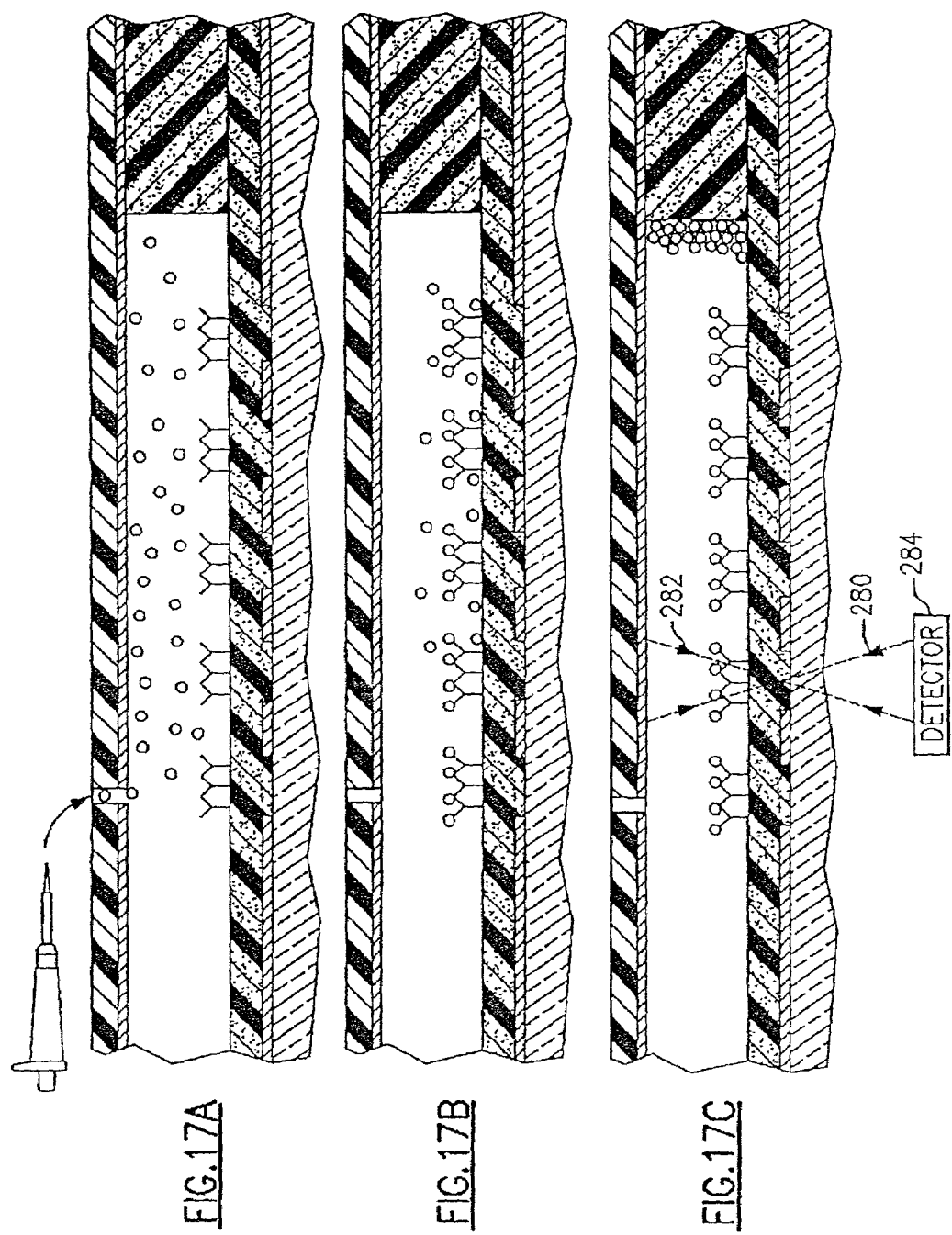

METHODS AND APPARATUS FOR BLOOD TYPING WITH OPTICAL BIO-DISC

CROSS-REFERENCES TO RELATED APPLICATIONS

This application claims the benefit of U.S. Provisional Application No. 60/249,477, filed Nov. 17, 2000, and U.S. Provisional Application No. 60/252,796, filed Nov. 22, 2000. These applications are hereby incorporated by reference into the subject application in their entireties.

FIELD OF THE INVENTION

The present invention relates to the field of diagnostic assays and biological analysis and to identification of cell types in a biological sample and analyses related thereto. The invention is further related to the manufacture and use of optically readable discs for biological analysis.

BACKGROUND OF THE INVENTION

Medical diagnostics are critical to the diagnosis and treatment of disease, as well as the general maintenance of good health. Particularly useful are the biological and chemical assays performed on whole blood or its components. One early area of development in the field related to blood typing for the purposes of transfusion. In 1901 Karl Landsteiner discovered that when the blood of one human being was transfused with that of another human being, differences in their blood might well be the cause of shock, jaundice, and the blood disorder hemoglobinuria that had resulted through earlier blood transfusions. Landsteiner classified human blood into A, B, and O groups and demonstrated that transfusions between humans of group A or B did not result in the destruction of new blood cells and that this catastrophe occurred only when a person was transfused with the blood of a person belonging to a different group. A fourth main blood type, AB was found in 1902 by A. Decastrello and A. Sturli.

From that time, differing blood typing systems have been devised. Historically the naming of blood grouping systems has been disorganized. The common conventions stipulating that dominant traits be given capital letters and recessive traits be designated with lower case letters have not been followed. Also by tradition, red cell antigens were given alphabetical designations or were named after the family of the antibody producer.

The International Society of Blood Transfusion (ISBT) (National Blood Service/Lancaster, PO Box 111, Royal Lancaster Infirmary, Ashton Road, Lancaster LA1 4GT, England) has instituted a numerical system of nomenclature to help standardize red cell blood group terminology. This convention mandates that each system and collection has been given a number and letter designation, and each antigen within the system is numbered sequentially in order of discovery. As of this writing, over 20 blood group systems and seven antigen collections have been defined.

The structure of the antigen determinants for the ABO blood typing system was established in the 1950s by Watkins and Morgan (Nature 180:1038-1040, 1957) and Kabat et al. (Blood Group Substrates: Their Chemistry and Immuno-Chemistry, 1956, Academics Press, New York). Numerous sera and isolated antibodies have been used for ABO blood typing purposes. For example, U.S. Pat. No. 4,764,465 to Foung et al. (1988) entitled "Human Monoclonal Antibody Against Group A Red Blood Cells" is directed to a human monoclonal antibody that directly agglutinates type A human red blood cells. The exemplified antibody is an IgM and is produced by hybrid cells lines S-H22 and HHA1.

More recently, genes encoding the antigenic determinants have also been identified. See for example U.S. Pat. No. 5,326,857 to Yamamoto et al. (1994) entitled "ABO Genotyping" which discloses genes defining the ABO histo-blood groups and methods for the identification of histo-blood group ABO status. The methods described include the use of DNA probes or size separation of DNA fragments unique to a blood group status, DNA constructs, recombinant methods for providing histo-blood glycosyltransferases, methods for tumor suppression, purified histo-blood group glycosyltransferases, and antibodies produced therefrom which bind to protein epitopes.

A variety of apparatuses have been utilized to perform ABO blood typing analysis. For example, U.S. Pat. No. 4,650,662 to Goldfinger et al. (1987) entitled "Portable Blood Typing Apparatus and Method" discloses a portable apparatus to enable rapid determination of an individual's ABO blood group and Rh blood type and a method of using such apparatus. The apparatus has a plurality of microtubes joined together which contain blood taken from an individual. The assembly of microtubes is connected during use to an assembly of reaction chambers containing blood typing reagents. The apparatus enables rapid visualization of the test reactions within the reaction chambers, and may be used in locations removed from a laboratory to determine the ABO blood group and Rh blood type of an individual.

U.S. Pat. No. 5,324,479 to Naldoni et al. (1994) entitled "Analyzer for the Determination of the Phenotype and the ABO Blood Group" discloses an analyzer for the determination of the ABO blood type of a patient. The analyzer comprises a rotatable plate carrying sample-bearing test-tubes and dilution test-tubes arranged along concentric circumferences; a dispensing needle which is movable by mechanical means between a washing position, a position for drawing a sample, a position for diluting the sample and a position for introducing the sample into a reading well; a station for washing said needle; a conveyor unit for conveying carrier members which are provided with 12 reaction wells to a position for receiving diluted or the undiluted samples from the dispensing needle; an automatic feeder that feeds small balls into each of the wells during the forward motion along the conveyor unit; mechanical means for transferring the carrier member to a reading zone; a unit that meters the specific antiserum or red cells into each one of the wells; and an optical reading device that horizontally reads the transmittance of each one of the wells, starting from the moment when antiserum or red cells are introduced; and a processor for functionally controlling the analyzer and for issuing an estimate of the results of the analyses.

U.S. Pat. No. 6,030,581 entitled "Laboratory In A Disc" (hereinafter "the '581 patent") describes an apparatus that includes an optical disc, having a substantially self contained assay means for binding an analyte suspected of being in a sample. U.S. Pat. No. 5,892,577 entitled "Apparatus and Method for Carrying Out Analysis of Samples" describes systems and methods for conducting an optical inspection of a biological, chemical or biochemical sample supported by an optical transparent disc.

U.S. Pat. No. 6,143,510, entitled "Measuring Method Using Whole Blood Sample" describes methods for quantitatively measuring analyte in an undiluted whole blood sample by contacting the sample with magnetic particles coated with a binding partner which binds to an analyte in the sample. There is no description of this assay being carried out on an optical bio-disc. In addition, U.S. Pat. No. 5,993,665, entitled "Quantitative Cell Analysis Methods Employing Magnetic Separation" describes immobilization of microscopic entities into a defined region in a collection chamber such that analysis by automated means is possible. The '665 patent describes quantitative collection of magnetically labeled target entities.

There remains a need in the art of medical diagnostics for more efficient and less expensive diagnostic techniques.

SUMMARY OF THE INVENTION

In a first aspect, the invention provides, a method for determining a blood group type of an individual by direct typing on an optical bio-disc comprising applying red blood cells to at least one chamber in the optical bio-disc, the chamber surface including at least one capture field including a capture antibody, at least one positive control field, and at least one negative control field; incubating the samples in the disc to promote antigen-antibody interaction; placing the disc into an optical reader that supports it on a first side; rotating the disc about an axis substantially perpendicular to the first side to separate non-captured cells from captured cells located on the chamber surface; obtaining a measurement for the test field, the positive control field, and the negative control field analyzing the measurement of the test field, the positive control field and the negative control field to determine blood group type of the individual. In certain embodiments of the first aspect, the capture antibody is an anti-IgG antibody or the capture antibody is an anti-IgM antibody.

In certain embodiments of the first aspect, the capture antibody is an antibody specific for a red blood cell antigen. In certain embodiments of this embodiment, the red blood cell antigen is an ABO system blood group antigen, the red blood cell antigen is an Rh system blood group antigen, the red blood cell antigen is an MNSs system blood group antigen, the red blood cell antigen is a P system blood group antigen, the red blood cell antigen is a Lutheran system blood group antigen, the red blood cell antigen is a Kell system blood group antigen, the red blood cell antigen is a Lewis system blood group antigen, the red blood cell antigen is a Duffy system blood group antigen, the red blood cell antigen is a Kidd system blood group antigen, the red blood cell antigen is a Fisher system blood group antigen or the red blood cell antigen is a blood group antigen from any other blood group.

In other certain embodiments, the optical bio-disc is a reflective disc or the optical bio-disc is a transmissive disc. In other embodiments of the first aspect, the optical bio-disc comprises a CD or a DVD.

In certain embodiments of this aspect, the optical bio-disc has software embedded therein and the analysis of the measurement profile is controlled by the software, resulting in a bar code displaying the blood group type of the individual.

In certain embodiments of the first aspect, the capture antibody is biotinylated and is bound to the test field by streptavidin bound thereto, or the capture antibody is bound to the test field by a second antibody bound to thereto or capture the second antibody is biotinylated and is bound to the test field by streptavidin bound thereto.

In other embodiments of the first aspect, the positive control field has a molecule on its surface that binds all cells.

In embodiments thereof, the molecule is a lectin. In another embodiment thereof, the molecule is gold.

In a second aspect, the invention provides, a method for determining the presence of antibodies to an ABO blood group in individual's blood sample by reverse-typing on an optical bio-disc including purifying serum from a blood sample; creating at least one sample by mixing serum with cells of a known ABO blood group; injecting at least one sample into at least one channel in the optical bio-disc, thereby delivering the sample onto a capture field including a cell binding molecule; incubating the sample on the capture field to allow the cells to bind to the cell binding molecule; placing the disc into an optical reader that supports it on a first side; rotating the disc about an axis substantially perpendicular to the first side; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine the presence of agglutinated cells bound on the capture field; and determining the presence of antibodies in the sample.

In certain embodiments of the second aspect, the creating step includes the creation of two samples, a first sample utilizing Type A1 cells and a second sample utilizing Type B cells. In certain embodiments of the second aspect, step (b) further comprises the creation of a sample with Type AB cells. In certain embodiments of the second aspect, the cell binding molecule is an anti-human immunoglobulin. In certain embodiments of the second aspect, the cell binding molecule is a lectin or the cell binding molecule is gold.

In certain embodiments of the second aspect, the optical bio-disc is a reflective disc or the optical bio-disc is a transmissive disc. In certain embodiments of the second aspect, the optical bio-disc comprises a CD or a DVD.

In a third aspect, the invention provides method for determining the presence of antibodies to an ABO blood group in an individual's blood sample by reverse-typing on an optical bio-disc comprising applying a blood sample to at least one microfluidic channel in the optical bio-disc including a separation chamber with at least one microfilter, at least one mixing chamber, and at least one capture chamber; spinning for a first time the disc at a first speed to effect separation of the blood sample into cells and serum in the separation chamber; spinning for a second time the disc at a second speed higher than the first, the second speed effecting movement of the serum through the microfluidic channel into a mixing chamber; adding cells of a known ABO blood group cells into the mixing chamber containing serum; spinning for a third time the disc in one direction and alternately in another direction at least once to effect mixing of the serum and the cells; incubating the cells in the serum for a sufficient period of time to allow antibody-antigen binding; spinning for a fourth time the disc at a third speed higher than the second, the third speed effecting movement of the cells into of a capture chamber, the capture chamber including surface with a molecule that binds cells; incubating the sample in the capture chamber to promote cell binding to the chamber surface; spinning the disc for a fifth time to remove non-bound cells from the capture field; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine the presence of agglutinated cells; and determining the presence of antibodies to a blood group in the sample.

In certain embodiments of the third aspect, there is a first mixing chamber connected to a first capture chamber and a second mixing chamber connected to a second capture chamber. In certain embodiments of the third aspect, Type A1 cells are placed in the first mixing chamber and Type B cells are placed in the second mixing chamber. In certain embodiments of this embodiment, the method further comprising a third mixing chamber connected to a third capture chamber and AB cells are added to the third mixing chamber in which AB cells are added.

In certain embodiments of the third aspect, the cell binding molecule is an anti-human immunoglobulin, the cell binding molecule is a lectin, or the cell binding molecule is gold. In certain embodiments of the third aspect, the optical bio-disc is a reflective disc or the optical bio-disc is a transmissive disc. In certain embodiments of the third aspect, the optical bio-disc comprises a CD or a DVD. In certain embodiments of the third aspect, the first speed is from about 1× to about 3×, the second speed is greater than 3× but less than about 5×, and the third speed is greater than about 5×. (1× refers to the audio standard for speed).

In a fourth aspect, the invention provides a method for determining the presence of antibodies to a blood group type in an individual by reverse-typing on an optical bio-disc comprising purifying serum from a blood sample; creating at least one sample by mixing serum with cells of a known blood group phenotyype; injecting at least one sample into at least one channel in the optical bio-disc, thereby delivering the sample onto a capture field including a cell binding molecule; incubating the sample on the capture field to allow the cells to bind to the cell binding molecule; placing the disc into an optical reader that supports it on a first side; rotating the disc about an axis substantially perpendicular to the first side; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine the presence of cells bound to the capture field; and determining the presence of blood group antibodies.

In certain embodiments of the fourth aspect, the cell binding molecule is an anti-human immunoglobulin. In other embodiments of this aspect, the optical bio-disc is a reflective disc the optical bio-disc is a transmissive disc. In certain embodiments of this aspect, the optical bio-disc comprises a CD or a DVD. In certain embodiments of the fourth aspect, the first speed is from about 1× to about 3×, the second speed is greater than 3× but less than about 5×, and the third speed is greater than about 5×.

In certain embodiments of the fourth aspect, the cells added are characterized as having at least one of the following: an ABO system blood group cell phenotype, an Rh system blood group cell phenotype, an MNSs system blood group cell phenotype, a P system blood group cell phenotype, a Lutheran system blood group cell phenotype, a Kell system blood group cell phenotype, a Lewis system blood group cell phenotype, a Duffy system blood group cell phenotype, a Kidd system blood group cell phenotype, a Fisher system blood group antigen or a red blood cell group antigen from any other group.

In a fifth aspect, the invention provides a method for determining the presence of antibodies to a blood group type in an individual's blood sample by antibody-typing on an optical bio-disc comprising applying a blood sample to at least one microfluidic channel in the optical bio-disc including a separation chamber with at least one microfilter, at least one mixing chamber, and at least one capture chamber; spinning for a first time the disc at a first speed to effect separation of the blood sample into cells and serum in the separation chamber; spinning for a second time the disc at a second speed higher than the first, the second speed effecting movement of the serum through the microfluidic channel into a mixing chamber; adding cells of a known blood group cell phenotype into the mixing chamber containing serum; spinning for a third time the disc in one direction and alternately in another direction at least once to effect mixing of the serum and the cells; incubating the cells in the serum for a sufficient period of time to allow antibody-antigen binding; spinning for a fourth time the disc at a third speed higher than the second, the third speed effecting movement of the cells into of a capture chamber, the capture chamber including a surface with an anti-human immunoglobulin molecule; incubating the sample in the capture chamber to promote cell binding to the chamber surface; spinning for a fifth time the disc to remove non-bound cells; scanning the chamber with an incident beam of electromagnetic radiation by rotating the disc about an axis substantially perpendicular to the first side by moving the incident beam in a direction radial to the axis; detecting a return beam of electromagnetic radiation formed by at least a part of the incident beam after interacting with the disc; converting the return beam into an output signal; analyzing the output signal to determine if the cells are bound; and determining the presence of blood group antibodies are in the sample.

In certain embodiments of this aspect, the cell binding molecule is a lectin or wherein the cell binding molecule is gold. In other certain embodiments of the fifth aspect, the optical bio-disc is a reflective disc or the optical bio-disc is a transmissive disc. In certain embodiments of this embodiment, the optical bio-disc comprises a CD or a DVD. In certain embodiments of this embodiment, the first speed is from about 1× to about 3×, the second speed is greater than 3× but less than about 5×, and the third speed is greater than about 5×.

In certain embodiments of the fifth aspect, the cells added are characterized as having at least one of the following an ABO system blood group cell phenotype, an Rh system blood group cell phenotype, an MNSs system blood group cell phenotype, a P system blood group cell phenotype, a Lutheran system blood group cell phenotype, a Kell system blood group cell phenotype, a Lewis system blood group cell phenotype, a Duffy system blood group cell phenotype, a Kidd system blood group cell phenotype, a Fisher system blood group antigen, or a red blood cell group antigen from any other blood group.

In a sixth aspect, the invention provides an apparatus for determining a blood group type of an individual. The apparatus includes an optical bio-disc including at least one capture chamber including a layer including a first capture antibody, and a layer including a second capture antibody bound by the first capture antibody, the second capture antibody being specific for a blood group antigen; a disc drive assembly; an optical reader; and software for blood group analysis.

In certain embodiments of the sixth aspect, the capture antibody is an anti-IgG antibody or the second capture antibody is an anti-IgM antibody. In certain embodiments of the sixth aspect, the capture antibody is an antibody specific for a red blood cell antigen. In certain embodiments of the latter embodiment, red blood cell antigen is an ABO system blood group antigen, the red blood cell antigen is an Rh system blood group antigen, the red blood cell antigen is an MNSs system blood group antigen, the red blood cell antigen is a P system blood group antigen, the red blood cell antigen is a Lutheran system blood group antigen, the red blood cell antigen is a Kell system blood group antigen, the red blood cell antigen is a Lewis system blood group antigen or the red blood cell antigen is a Duffy system blood group antigen, the red blood cell antigen is a Kidd system blood group antigen, the red blood cell antigen is a Fisher system blood group antigen, or a red blood cell group antigen from any other group. In certain embodiments of the sixth aspect, the optical bio-disc is a reflective disc or the optical bio-disc is a transmissive disc or the optical bio-disc comprises a CD or a DVD.

In an seventh aspect, the invention provides an optical-bio disc for performing a blood-typing assay. The bio-disc includes a substrate; a separation chamber associated with the substrate, the separation chamber including first inlet port; filter means associated with the separation chamber; a first mixing chamber in fluid communication with the separation chamber, the first mixing chamber including a second inlet port; a second mixing chamber in fluid communication with the separation chamber, the second mixing chamber including a third inlet port; a first detection chamber in fluid communication with the first mixing chamber, the first detection chamber including a capture zone; and a second detection chamber in fluid communication with the second mixing chamber, the second detection chamber including a capture zone. In certain embodiments of the seventh aspect, the optical bio-disc does not contain a second inlet port leading to the mixing chamber.

In certain embodiments of the seventh aspect, when a sample of blood is directed into the separation chamber through the inlet port and the disc is rotated at a first speed, the filter means separates white blood cells, red blood cells, and platelets from the blood sample to provide a sample of serum. In a further embodiment, when the disc is rotated at a second speed, the sample of serum is directed into the first and second mixing chambers. In another embodiment, the inlet port of the first mixing chamber is employed to direct cells of a first type into the first mixing chamber, and the inlet port of the second mixing chamber is employed to direct cells of a second type into the second mixing chamber. In other certain embodiments, when the disc is rotated at a third speed, a mixture of serum and cells of the first type is directed into the first detection chamber, and a mixture of serum and cells of the second type is directed into the second detection chamber.

Certain embodiments of the seventh aspect provide for disc rotation in a predetermined manner to mix the cells of the first type with serum in the first mixing chamber, and mix the cells of the second type with serum in the second mixing chamber. In certain embodiments, the predetermined manner of rotating the disc includes alternately rotating the disc in one direction and then an opposite direction to thereby create an agitation action to promote mixing of serum and cells.

In certain embodiments of the seventh aspect, the capture zone in the first detection chamber includes a first type of capture agent implemented to capture specific cells having any affinity therefor. In other certain embodiments, the capture zone in the second detection chamber includes a second type of capture agent implemented to capture specific cells having any affinity therefor.

In certain embodiments of the seventh aspect, an incident beam of radiant energy is directed into the first detection chamber to determine whether any cells were captured by the first type of capture agent. In other embodiments, an incident beam of radiant energy is directed into the second detection chamber to determine whether any cells were captured by the second type of capture agent.

In certain embodiments of the seventh aspect, the first type of capture agent is an anti-human immunoglobulin having an affinity for an antibody bound to the cells or a non-cell specific molecule that binds a molecule on the surface of all red blood cells. In certain embodiments of the seventh aspect, the second type of capture agent is an anti-human immunoglobulin having an affinity for an antibody bound to the cells or a non-cell specific molecule that binds a molecule on the surface of all red blood cells.

In certain embodiments of the seventh aspect, the separation chamber, the first and second mixing chambers, and the first and second detection chambers are formed in the substrate. In other certain embodiments of the seventh aspect, the separation chamber, the first and second mixing chambers, and the first and second detection chambers are formed in a cap bonded to the substrate. In yet other certain embodiments of the seventh aspect, the separation chamber, the first and second mixing chambers, and the first and second detection chambers are formed in a channel layer bonded between a cap portion and the substrate. In certain embodiments of the seventh aspect, the separation chamber, the first and second mixing chambers, and the first and second detection chambers are partially formed in a cap portion and partially formed in the substrate, the cap portion and the substrate being bonded together in register to thereby fully form the chambers.

In certain embodiments of the seventh aspect, the optical bio-disc further includes information encoded in an information layer readable by a disc drive. In certain embodiments thereof, the encoded information is used to rotate the disc in a prescribed manner. In certain embodiments of the seventh aspect, the information layer is reflective. In yet other embodiments of this aspect, the information layer is semi-reflective.

In an eighth aspect, the invention provides a method for manufacturing a disc comprising: providing over a substrate of the disc an encoded informational layer; forming target areas; providing a capture layer in the target areas; attaching at least one capture agen. In certain embodiments, the encoded informational layer is a reflective layer, annd the target areas are regions etched from the reflective layer. In certain embodiments, the encoded informational layer is a partially reflective and partially transmissive layer, and the target areas are regions adjacent the informational layer.

The above described and many other features and attendant advantages of the present invention will become better understood by reference to the following detailed description when taken in conjunction with the accompanying drawings.

BRIEF DESCRIPTION OF THE DRAWINGS

FIGS. 3A–3C are an exploded perspective view, top view, and partially cut-away perspective views, respectively, of a transmissive disc according to an embodiment of the present invention.

FIG. 5 is a pictorial presenting a general schematic of the cell capture technologies of the invention.

FIG. 7A–F is a schematic presenting a series of cross sections demonstrating the preparation of one example of a bio-disc of the invention.

FIG. 11C depicts the incident beam aimed at the capture field.

FIG. 12C depicts the incident beam aimed at the capture field.

FIG. 16 is a pictorial presenting the events of cell binding during the reverse typing test when antibodies to an ABO/Rh blood group antigen are present. FIG. 16C depicts the incident beam aimed at the capture field.

FIG. 17 is a pictorial presenting the events of cell binding during the reverse typing test when no antibodies to an ABO/Rh blood group antigen are present. FIG. 17A shows red blood cells that are not agglutinated after contact with serum. FIG. 17B shows the same red blood cells interacting the capture field. FIG. 16C shows the capture of single cells (i.e., non-agglutinated) red blood cells by a molecule, e.g., a lectin, that binds all cells irrespective of antibody binding. An incident beam of electromagnetic radiation is striking the capture field.

DETAILED DESCRIPTION OF THE INVENTION

The patents and publications cited herein reflect the level of knowledge in the art and are hereby incorporated by reference in their entirety. Any conflict between any teaching of such references and this specification shall be resolved in favor of the latter.

Figure 1:
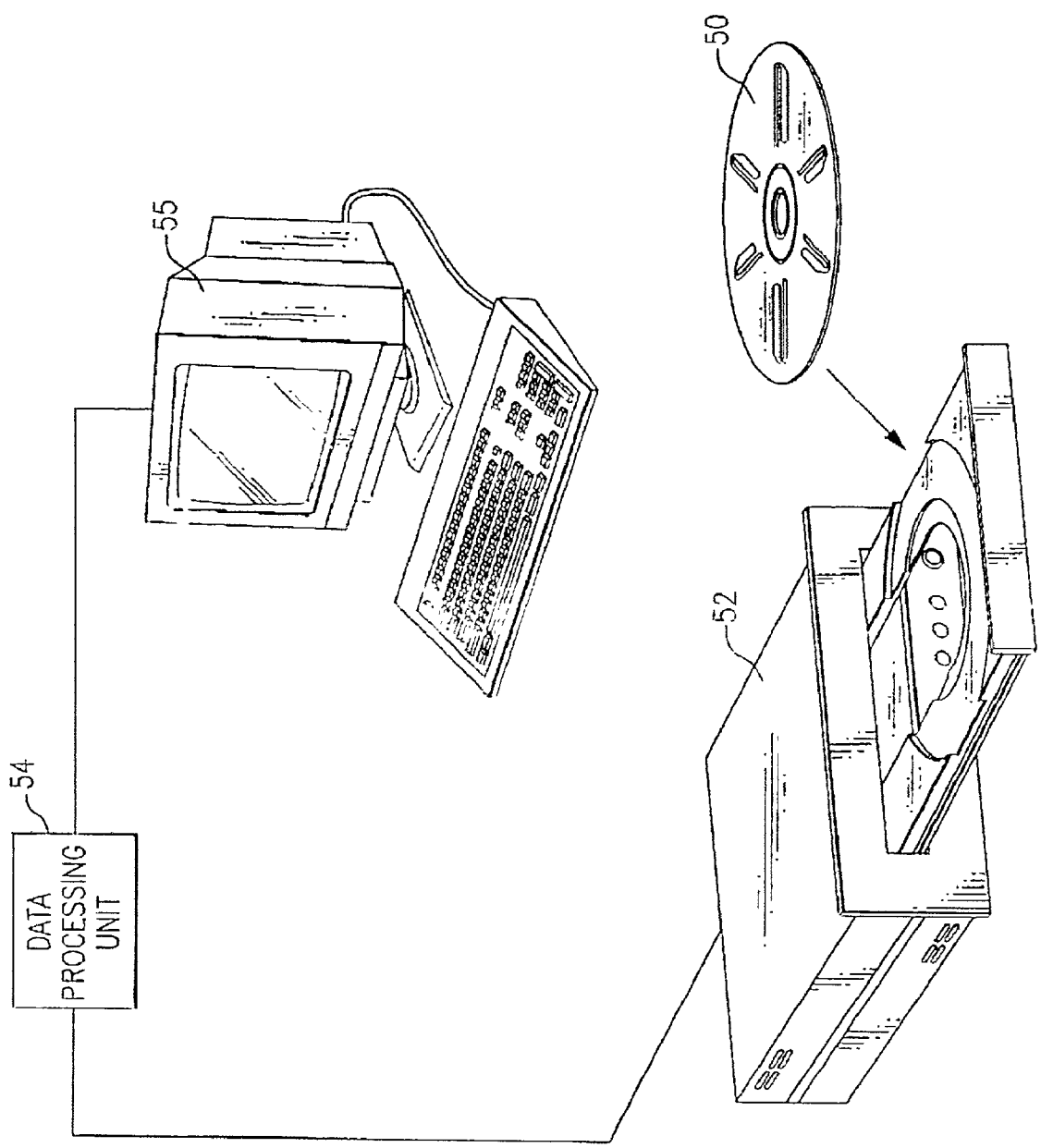
FIG. 1 is a pictorial presenting the integrated optical bio-disc with sample chambers, an optical disc drive for sample processing and data collection, a data processing unit, and a monitor.

The invention described herein provides diagnostic assays based on cell-capture technology adapted to an optical bio-disc and methods and compositions related thereto. Referring to FIG. 1, the system utilizes an optical bio-disc 50, an optical detection system 52, a data processing unit 54, and a monitor 55 to display output results. The cost-benefit of the biological assays of the present invention is that the cost of an analysis of a sample can be as low as 7 cents, which is much less expensive than a test run in a clinical setting. The methods described herein are capable of being carried out by a relatively unskilled person in almost any location. The person would only need to be able to obtain a biological sample, e.g., whole blood, from an individual. In addition, a series of tests can be performed on one sample on a single disc, which increases the cost and time efficiency of the analysis.

The assays described herein can replace those now routinely carried out in clinical laboratories such as hospitals and service laboratories; those carried out at the point of patient care (e.g., in physician offices, in patient service centers, and in emergency vehicles/rooms). The methods of the present invention can be used as portable testing and detection systems. Important features of this technology are that it is (1) extremely low cost as to both the instrumentation and the necessary reagents, (2) it is fast, highly sensitive and reproducible, highly accurate, and (3) many assays can be carried out simultaneously.

Optical Bio-Disc

An optical bio-disc for use with embodiments of the present invention may have any suitable shape, diameter, or thickness, but preferably is implemented on a round disc with a diameter and a thickness similar to those of a compact disc (CD), a recordable CD (CD-R), CD-RW, a digital versatile disc (DVD), DVD-R, DVD-RW, or other standard optical disc format. The disc may include encoded information, preferably in a known format, for performing, controlling, and post-processing a test or assay, such as information for controlling the rotation rate of the disc, timing for rotation, stopping and starting, delay periods, multiple rotation steps, locations of samples, position of the light source, and power of the light source. Such encoded information is referred to generally as operational information. Alternatively, the operational information can be provided separately.

The disc may be reflective, transmissive, or some combination of reflective and transmissive. In the case of a reflective disc, an incident light beam is focused onto a reflective surface of the disc, reflected, and returned through optical elements to a detector on the same side of the disc as the light source. In a transmissive disc, light passes through the disc (or portions thereof) to a detector on the other side of the disc from the light source. In a transmissive portion of a disc, some light may also be reflected and detected as reflected light.

Figure 2A:
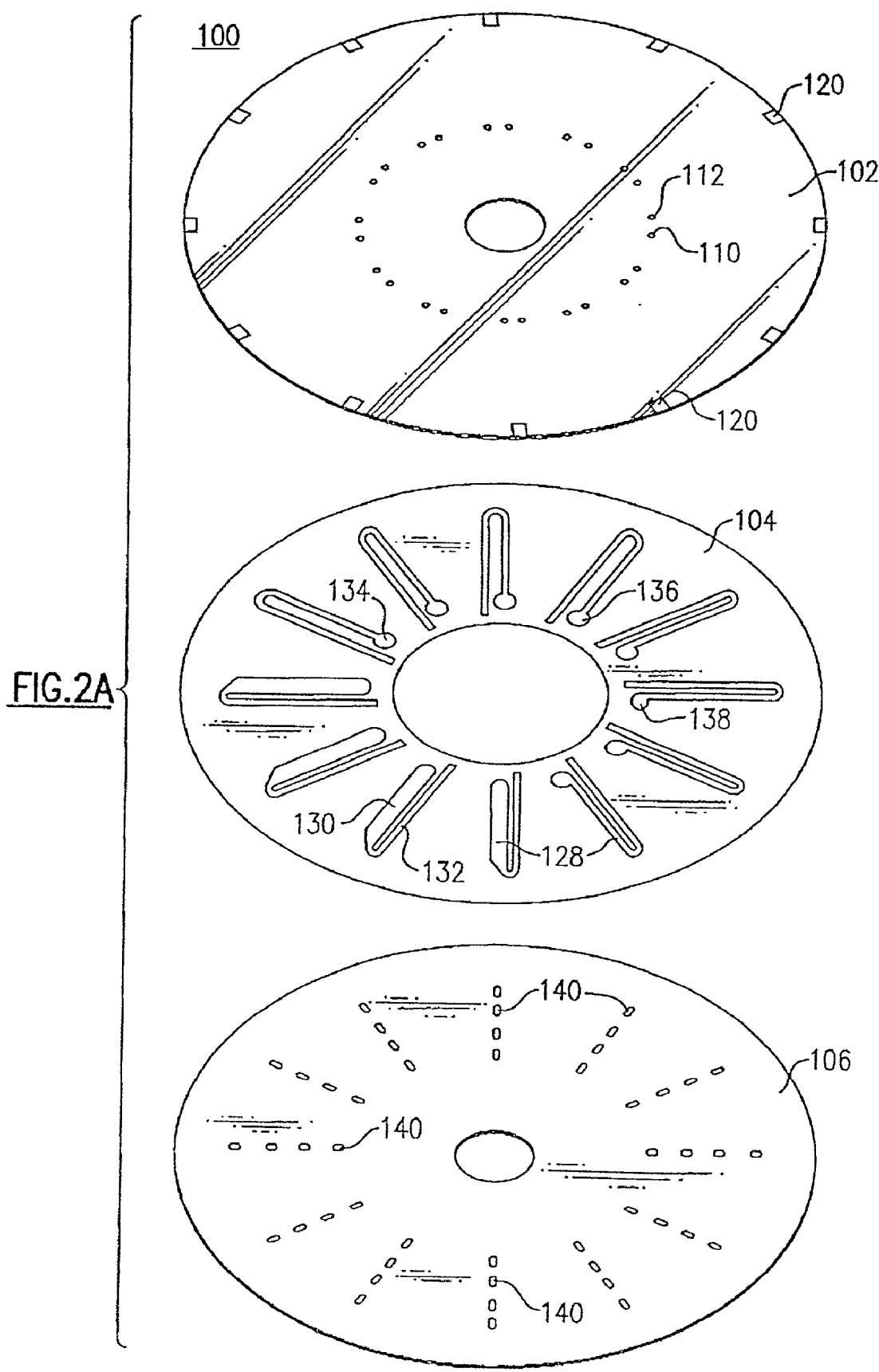
FIGS. 2A–2C are an exploded perspective view, top view, and partially cut-away perspective views, respectively, of a reflective disc according to an embodiment of the present invention.
Figure 2B:
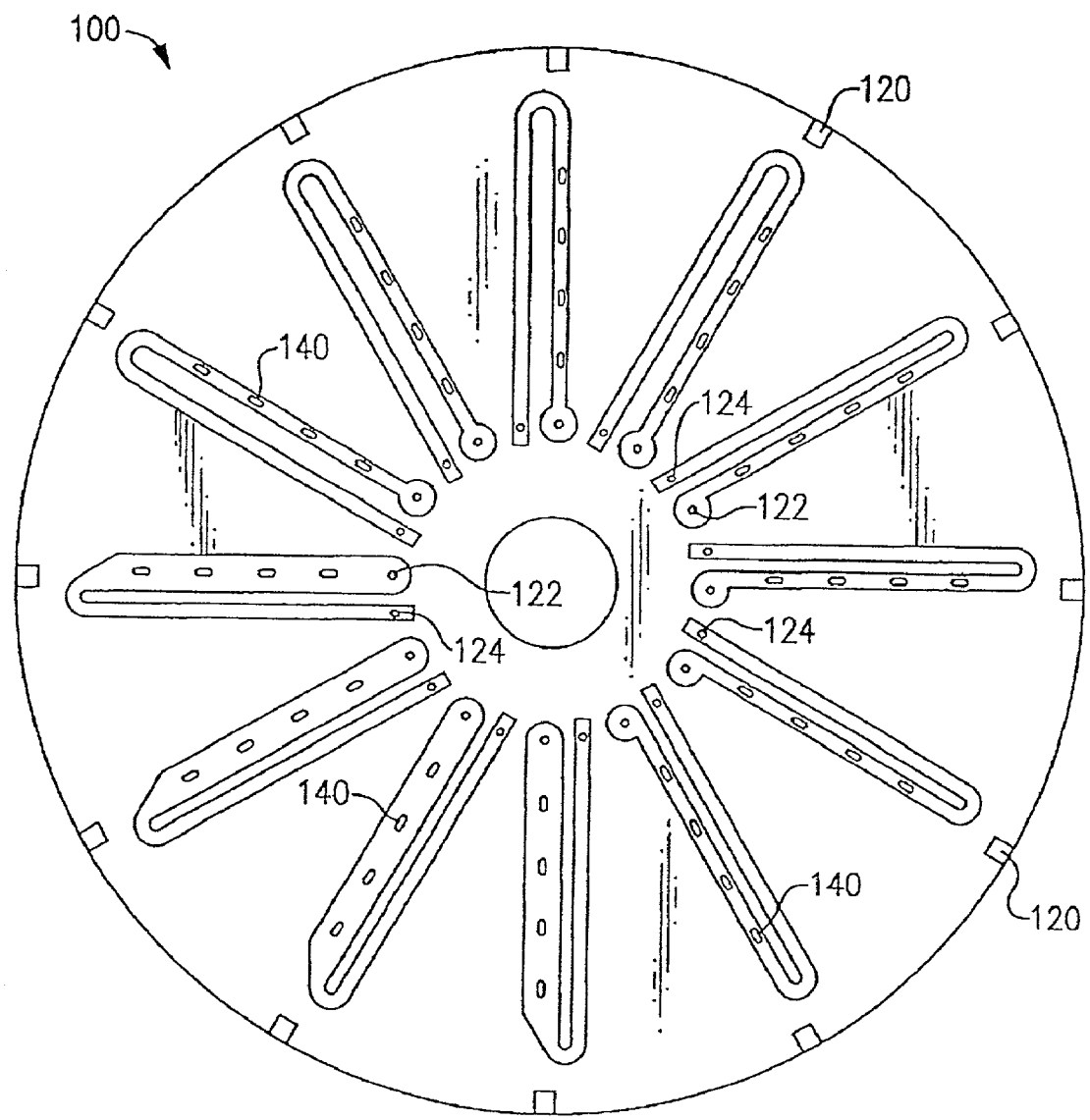
Figure 2C:
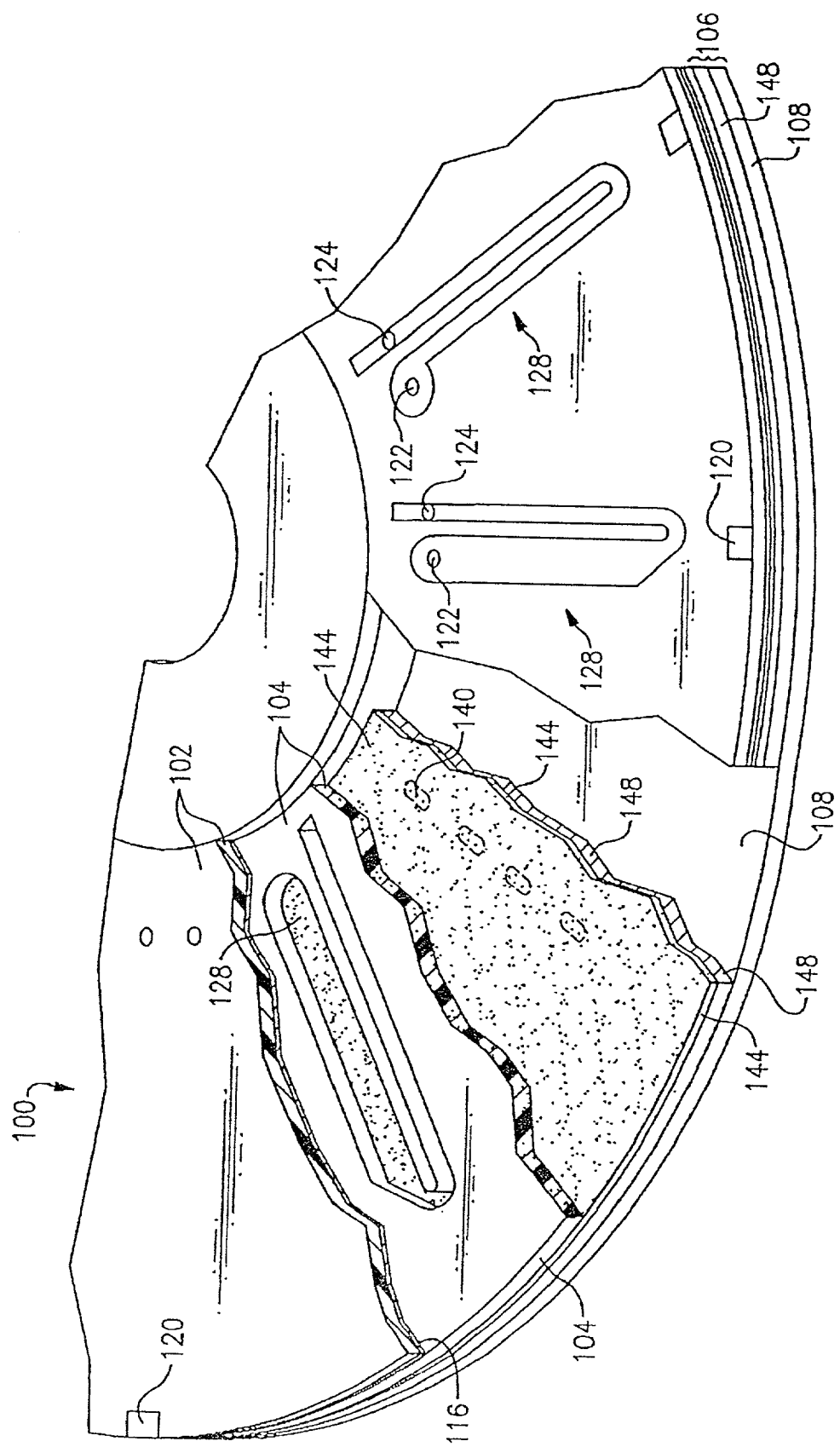

Referring to FIGS. 2A, 2B, and 2C, a reflective disc 100 is shown with a cap 102, a channel layer 104, and a substrate 106. Cap 102 has inlet ports 110 for receiving samples and vent ports 112. Cap 102 may be formed primarily from polycarbonate, and may be coated with a reflective layer 116 on the bottom thereof. Reflective layer 116 is preferably made from a metal, such as aluminum or gold.

Channel layer 104 defines fluidic circuits 128 by having desired shapes from channel layer 104. Each fluidic circuit 128 preferably has a flow channel 130 and a return vent channel 132, and some have a mixing chamber 134. A mixing chamber 136 can be symmetrically formed relative to the flow channel 130, while an off-set mixing chamber 138 is formed to one side of the flow channel 130. Fluidic circuits 128 can include other channels and chambers, such as preparatory regions or a waste region, as shown, for example, in U.S. Pat. No. 6,030,581, which is incorporated herein by reference. Channel layer 104 can include adhesives for bonding substrate to cap.

Substrate 106 has polycarbonate layer 108, and has target zones 140 formed as openings in a reflective layer 148 deposited on the top of layer 108. Target zones 140 may be formed by removing portions of reflective layer 148 in any desired shape, or by masking target zone areas before applying reflective layer 148. Reflective layer 148 is preferably formed from a metal, such as aluminum or gold, and can be configured with the rest of the substrate to encode operational information that is read with incident light, such as through a wobble groove or through an arrangement of pits. Light incident from under substrate 106 thus is reflected by layer 148, except at target zones 140, where it is reflected by layer 116.

Referring particularly to FIG. 2C, optical disc 100 is cut away to illustrate a partial cross-sectional view. An active capture layer 144 is formed over reflective layer 148. Capture layer 144 may be formed from nitrocellulose, polystyrene, polycarbonate, gold, activated glass, modified glass, or a modified polystyrene, for example, polystyrene-co-maleic anhydride. Channel layer 104 is over capture layer 144.

Trigger marks 120 are preferably included on the surface of a reflective layer 148, and may include a clear window in all three layers of the disc, an opaque area, or a reflective or semi-reflective area encoded with information. These are discussed below.

In operation, samples are introduced through inlet ports 110 of cap 102. When rotated, the sample moves outwardly from inlet port 110 along capture layer 144. Through one of a number of biological or chemical reactions or processes, detectable features may be present in the target zones. These features are referred to as investigational features. Examples of such processes are shown in the incorporated U.S. Pat. No. 6,030,581.

The investigational features captured by the capture layer may be designed to be located in the focal plane coplanar with reflective layer 148, where an incident beam is typically focused in conventional readers; alternatively, the investigational features may be captured in a plane spaced from the focal plane. The former configuration is referred to as a "proximal" type disc, and the latter a "distal" type disc.

Figure 3B:
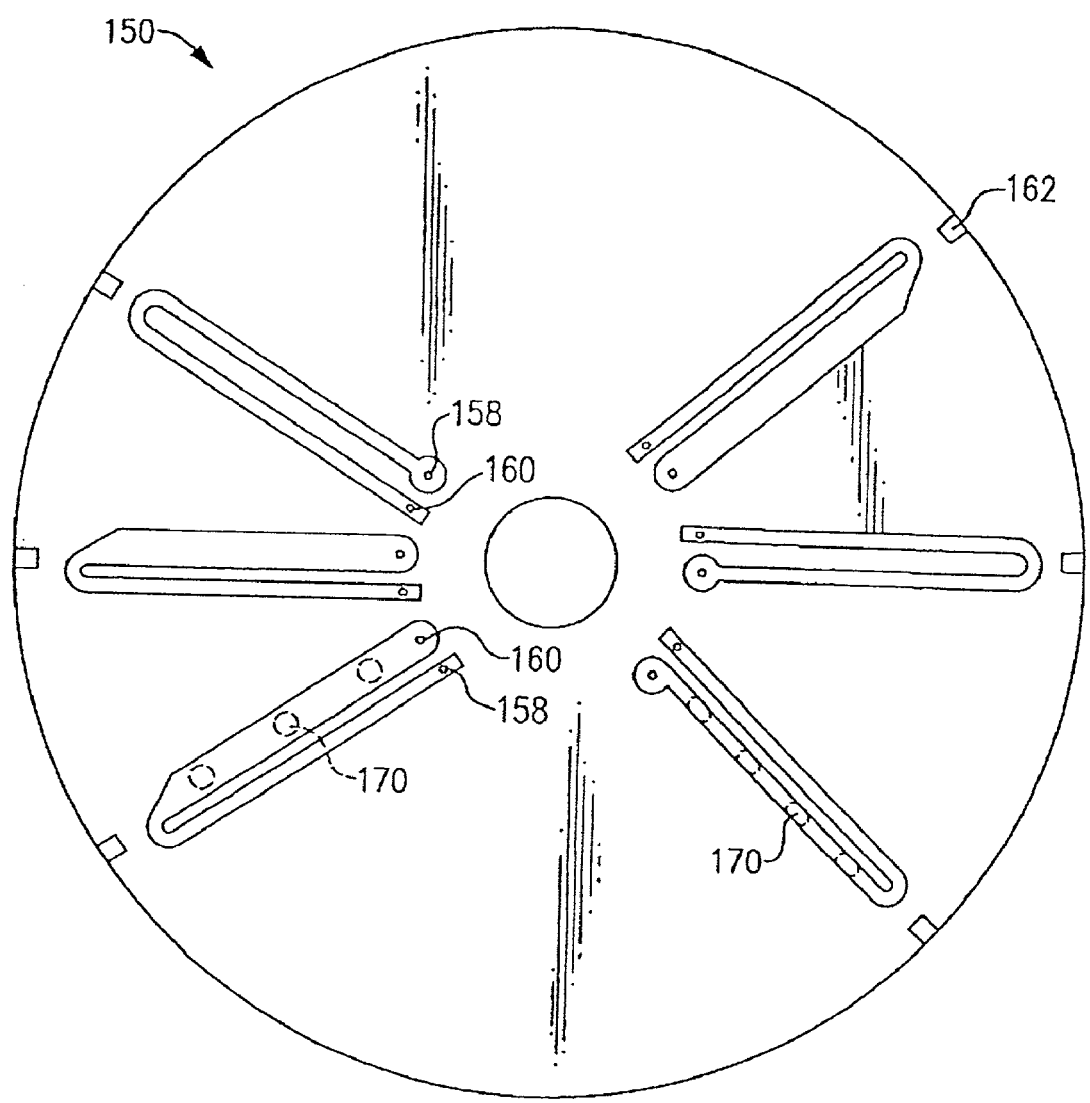
Figure 3C:
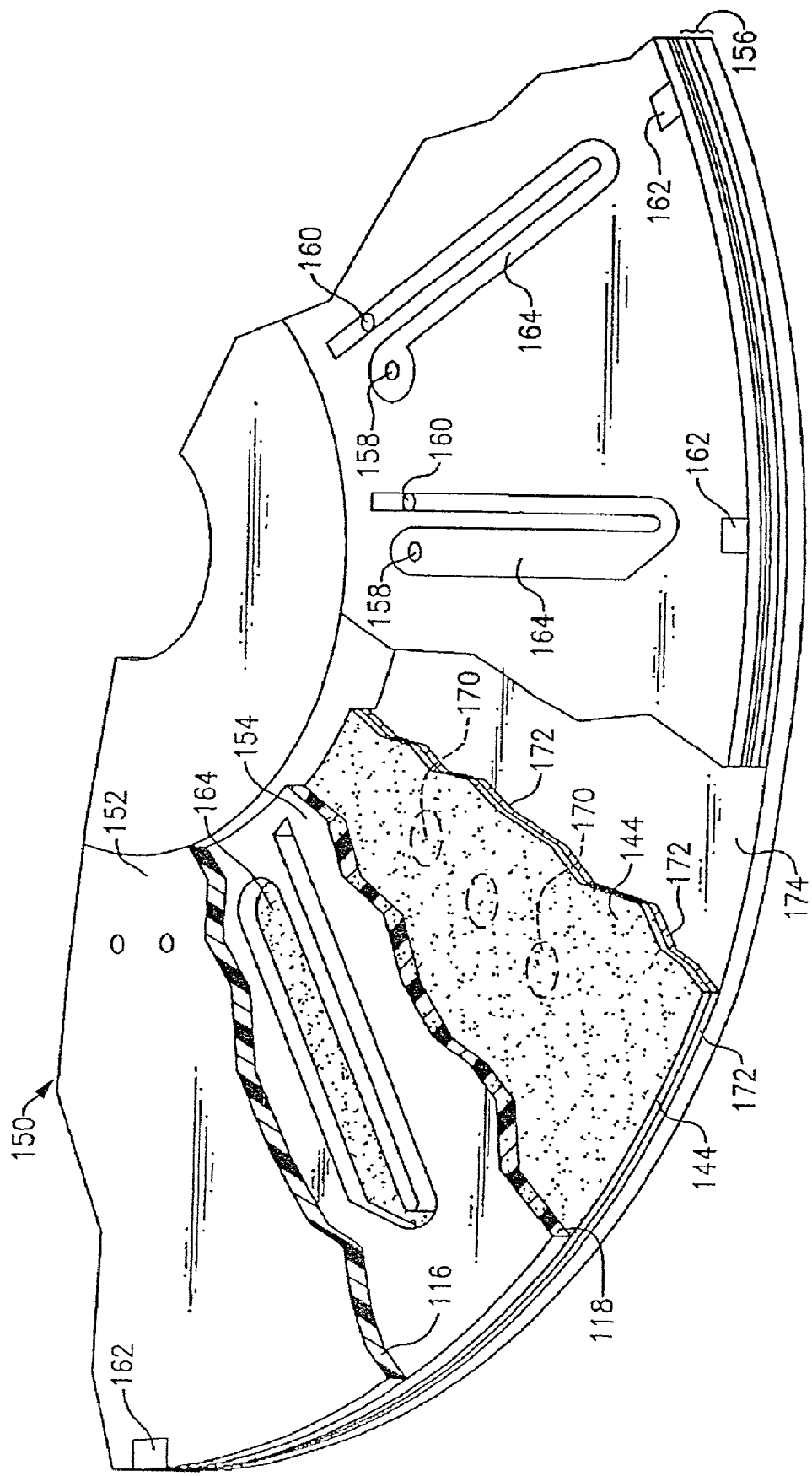

Referring to FIGS. 3A, 3B, and 3C, a transmissive optical disc 150 has a cap 152, a channel layer 154, and a substrate 156. Cap 152 includes inlet ports 158 and vent ports 160 and is preferably formed mainly from polycarbonate. Trigger marks 162 similar to those for disc 100 may be included. Channel layer 154 has fluidic circuits 164, which can have structure and use similar to those described in conjunction with FIGS. 2A, 2B, and 2C.

Substrate 156 may include target zones 170, and preferably includes polycarbonate layer 174. Substrate 156 may, but need not, have a thin semi-reflective layer 172 deposited on top of layer 174. Semi-reflective layer 172 is preferably significantly thinner than reflective layer 148 on substrate 106 of reflective disc 100 (FIGS. 1A–1C). Semi-reflective layer 172 is preferably formed form a metal, such as aluminum or gold, but is sufficiently thin to allow a portion of an incident light beam to penetrate and pass through layer 172, while some of the incident light is reflected back. A gold film layer, for example, is 95% reflective at a thickness greater than about 700 Å, while the transmission of light through the gold film is about 50% transmissive at approximately 100 Å.

FIG. 3C is a cut-away perspective view of disc 150. The semi-reflective nature of layer 172 makes its entire surface available for target zones, including virtual zones defined by trigger marks or specially encoded data patterns on the disc. Target zones 170 may also be formed by marking the designated area in the indicated shape or alternatively in any desired shape. Markings to indicate target zone 170 may be made on semi-reflective layer 172 or on a bottom portion of substrate 156 (under the disc). Target zones 170 may be created by silk screening ink onto semi-reflective layer 172.

An active capture layer 180 is applied over semi-reflective layer 172. Capture layer 180 may be formed from the same materials as described above in conjunction with layer 144 (FIG. 2C) and serves substantially the same purpose when a sample is provided through an opening in disc 150 and the disc is rotated. In transmissive disc 150, there is no reflective layer comparable to reflective layer 116 in reflective disc 100 (FIG. 2C).

Optical Disc Drive

Figure 4:
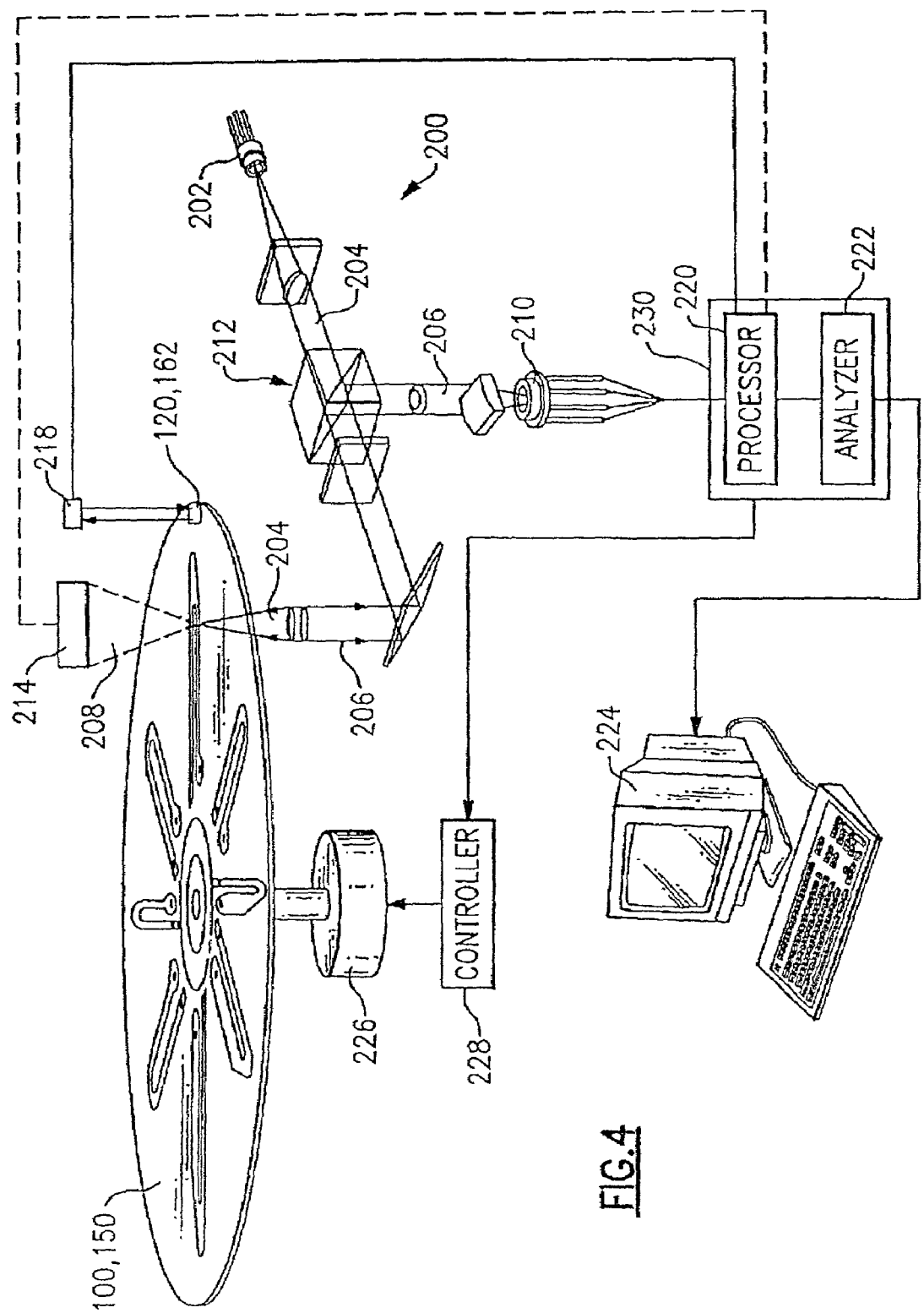
FIG. 4 is a pictorial and schematic diagram of an optical disc reading system according to an embodiment of the present invention.

FIG. 4 shows an optical disc reader system 200. This system may be a conventional reader for CD, CD-R, DVD, or other known comparable format, a modified version of such a drive, or a completely distinct dedicated device. The basic components are a motor for rotating the disc, a light system for providing light, and a detection system for detecting light.

A light source 202 provides light to optical components 212 to produce an incident light beam 204, a return beam 206, and a transmitted beam 208. In the case of reflective disc 100, return beam 206 is reflected from either reflective surface 148 or 116. Return beam 206 is provided back to optical components 212, and then to a bottom detector 210. For transmissive disc 150, a transmitted beam 208 is detected by a top detector 214. Optical components 212 can include a lens, a beam splitter, and a quarter wave plate that changes the polarization of the light beam so that the beam splitter directs a reflected beam through the lens to focus the reflected beam onto the detector. An astigmatic element, such as a cylindrical lens, may be provided between the beam splitter and detector to introduce astigmatism in the reflected light beam.

Data from detector 210 and/or detector 214 is provided to a computer 230 including a processor 220 and an analyzer 222. An image or output results can then be provided to a monitor 224. Computer 230 can represent a desktop computer, programmable logic, or some other processing device, and also can include a connection (such as over the Internet) to other processing and/or storage devices. A drive motor 226 and a controller 228 are provided for controlling the rotation and direction of disc 100 or 150. Controller 228 and the computer with processor 220 can be in communication or can be the same computer. Methods and systems for reading such a disc are also shown in Gordon, U.S. Pat. No. 5,892,577, which is incorporated herein by reference.

A hardware trigger sensor 218 may be used with either a reflective or transmissive disc. Triggering sensor 218 provides a signal to computer 230 (or to some other electronics) to allow for the collection of data by processor 220 only when incident beam 204 is on a target zone. Alternatively, software read from a disc can be used to control data collection by processor 220 independent of any physical marks on the disc.

The substrate layer may be impressed with a spiral track that starts at an innermost readable portion of the disc and then spirals out to an outermost readable portion of the disc. In a non-recordable CD, this track is made up of a series of embossed pits with varying length, each typically having a depth of approximately one-quarter the wavelength of the light that is used to read the disc. The varying lengths and spacing between the pits encode the operational data. The spiral groove of a recordable CD-like disc has a detectable dye rather than pits. This is where the operation information, such as the rotation rate, is recorded. Depending on the test, assay, or investigational protocol, the rotation rate may be variable with intervening or consecutive periods of acceleration, constant speed, and deceleration. These periods may be closely controlled both as to speed and time of rotation to provide, for example, mixing, agitation, or separation of fluids and suspensions with agents, reagents, antibodies, or other materials.

Numerous designs and configurations of an optical pickup and associated electronics may be used in the context of the embodiments of the present invention. Further details and alternative designs for compact discs and readers are described in Compact Disc Technology, by Nakajima and Ogawa, IOS Press, Inc. (1992); The Compact Disc Handbook, Digital Audio and Compact Disc Technology, by Baert et al. (eds.), Books Britain (1995); and CD-Rom Professional's CD-Recordable Handbook: The Complete Guide to Practical Desktop CD, Starrett et al. (eds.), ISBN: 0910965188 (1996); all of which are incorporated herein in their entirety by reference.

The disc drive assembly is thus employed to rotate the disc, read and process any encoded operational information stored on the disc, analyze the liquid, chemical, biological, or biochemical investigational features in an assay region of the disc, to write information to the disc either before or after the material in the assay zone is analyzed by the read beam of the drive or deliver the information via various possible interfaces, such as Ethernet to a user, database, or anywhere the information could be utilized.

The invention relates to clinical diagnostic assays based on cell-capture technology as employed on an optical bio-disc described herein. Various embodiments of this aspect of the invention are directed to blood-typing diagnostic assays.

In various aspects of the invention, a sample is loaded into a chamber within the optical bio-disc, where a capture field having bio-active capture agent is affixed thereto. The bio-disc is then subjected to conditions suitable for cell binding. Then, the bio-disc is placed into a CD drive assembly and is spun radially at a speed sufficient to separate unbound cells from bound cells, e.g., about 1000 rpm to about 4000 rpm for about one to five minutes. This spinning causes the cells which are not bound by the capture agent to be removed from the capture fields and collected in a separate part of the chamber (e.g., in a waste receptacle in the chamber).

As used herein, the term "capture field" encompasses target zone 170 of an optical bio-disc which has attached thereto, either directly or indirectly, a capture agent. The capture field is a discrete location on the surface having defined limits, metes and bounds.

As used herein, the term "capture agent" is a molecule A on the surface of the target zone 170 that recognizes a molecule B and binds with specificity thereto. The phrase "binds with specificity" is meant herein to refer to the binding of molecule A to molecule B by at least two fold, at least five fold, at least 10 fold, at least one hundred fold, at least 1000 fold, at least 10,000 fold or more when compared to other molecules that may be present in a biological sample. By way of non-limiting example, molecules that specifically recognize and bind to other molecules include antibodies, ligands, receptors, enzymes, substrates, biotin, avidin, and lectins The bioactive agent of the invention may be obtained from any source, including but not limited to viral, bacterial, fungal, plant, animal, in vitro or synthetically produced materials.

In certain embodiments of the invention, the capture agent is a capture antibody and the capture field has at least one capture antibody bound thereto. As used herein, the term "antibody" includes polyclonal, monoclonal, and recombinantly created antibodies. Antibodies of the invention can be produced in vivo or in vitro. Methods for the production of antibodies are well known to those skilled in the art. For example, see *Antibody Production: Essential Techniques*, Peter Delves (Ed.), John Wiley & Son Ltd, ISBN: 0471970107 (1997). Alternatively, antibodies may be obtained from commercial sources, e.g., Research Diagnostics Inc., Pleasant Hill Road, Flanders, N.J. 07836, Ortho Diagnostic Systems, BioClone Anti-A, Immucor, etc.)

The selection of a capture agent to be bound to a capture field is within the skill of those in the art. By way of non-limiting example, a receptor-specific ligand may be bound to a capture field for the purpose of binding cells expressing the receptor recognized by the ligand or a capture field may be bound by a lectin that binds specifically a sugar moiety expressed on the surface of a select population of cells for the purpose of binding those cells. Alternatively, the capture field may be bound by a capture antibody specific for a receptor on the surface of a cell. Thus, the invention provided herein is easily adapted to any number of biological assays.

The term "antibody" is not meant to be limited to antibodies of any one particular species, e.g., human, mouse, rat, goat, etc., are all contemplated by the invention. The term "antibody" is also inclusive of any class or subclass of antibodies, as all antibody types may be used to bring about an agglutination reaction. By way of non-limiting example, the IgG antibody class may be used for agglutination purposes or, if a higher antibody polyvalency is desired, the IgM class of antibodies may be utilized for the same purpose. Other types of immunoglobulins that bind specifically to cells are also included within the scope of the invention. Antibody fragments can also be utilized as a capture agent of the invention. The use of antibodies in the art of medical diagnostics is well known to those skilled in the art. For example, see Diagnostic and Therapeutic Antibodies (Methods in Molecular Medicine), Andrew J. T. George and Catherine E. Urch (Eds.), Humana Press; ISBN: 0896037983 (2000) and Antibodies in Diagnosis and Therapy: Technologies, Mechanisms and Clinical Data (Studies in Chemistry Series), Siegfried Matzku and Rolf A. Stahel (Eds.), Harwood Academic Pub.; ISBN: 9057023105 (1999), which are incorporated herein in their entirely by reference.

The capture field with the capture agent bound thereto can be structured in any way suitable to bind cells. In certain embodiments of the invention, one or more capture agents can be directly linked to the capture field. Thus, capture fields may be uniformly bound with a multiple copies of a single capture agent or, alternatively, capture fields may be bound with multiple copies of two or more capture agents to increase the specificity of the binding reaction. In other embodiments, the capture agent can be indirectly linked to the capture field. By way of non-limiting example, a capture field may be coated with a protein such as streptavidin and a capture agent such as an antibody can be linked to the streptavidin by way of a biotin moiety attached to the antibody.

In certain embodiments of the invention, the capture field of the invention has a first capture agent bound thereto and the first capture agent binds a second capture agent. By way of non-limiting example, an anti-IgM IgG antibody can serve as a first capture agent bound to a capture field, which itself binds an IgM antibody, the second capture agent. Thus, the capture agent bound to a capture field can in certain embodiments comprise more than one capture agent linked to one another in tandem.

Figure 6:
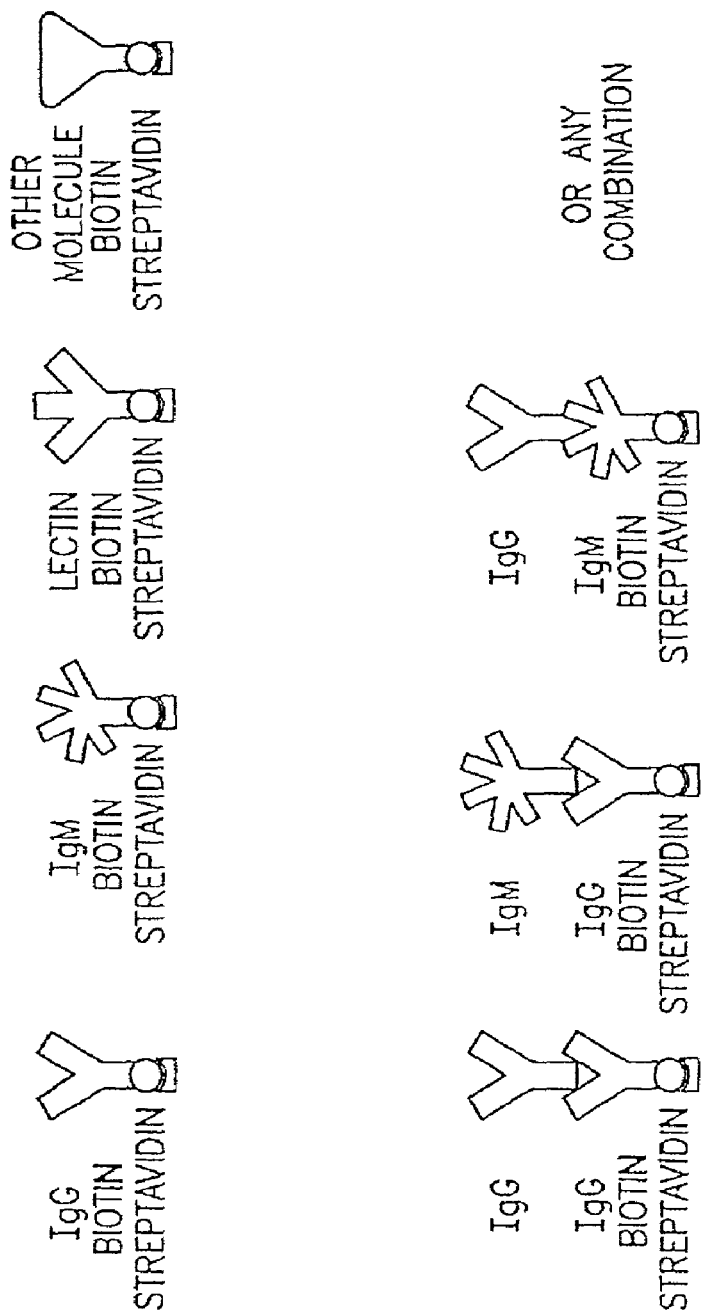
FIG. 6 is a pictorial schematic presenting the biotin/streptavidin-based cell capture technologies of the invention.

In various aspects of the invention, the capture agents may be attached to the capture field in different ways. By way of non-limiting example, various constructions are presented in Table 1.

capture technology of the invention are illustrated in FIGS. 5 and 6. FIG. 5 demonstrates various capture agents attached to a capture field by various means. By way of non-limiting example, IgG, IgM, a lectin, or another type of cell binding molecule can be bound directly to a capture field. Alternatively, the capture agents of the invention can be linked in tandem to the capture field to facilitate capture agent availability and minimize steric hindrance for cell capture. IgG and IgM can serve as anchors for any one of capture agents IgG, IgM, a lectin, or another molecule that binds cells for the purpose of capture. Many variations are possible for the capture technology of the invention, the latter provided exemplary embodiments thereof.

In one particular embodiment, FIG. 6 presents cell capture technology of the invention based on the strong recognition and binding of the streptavidin (or variants thereof) and biotin molecules. The bioactive agent streptavidin can be first applied to the capture field. This molecule can then be used to bind and hold capture various capture agents, e.g., biotinylated IgG or biotinylated IgM or biotinylated lectin or another cell binding molecule that is biotinylated.

Figure 7E:
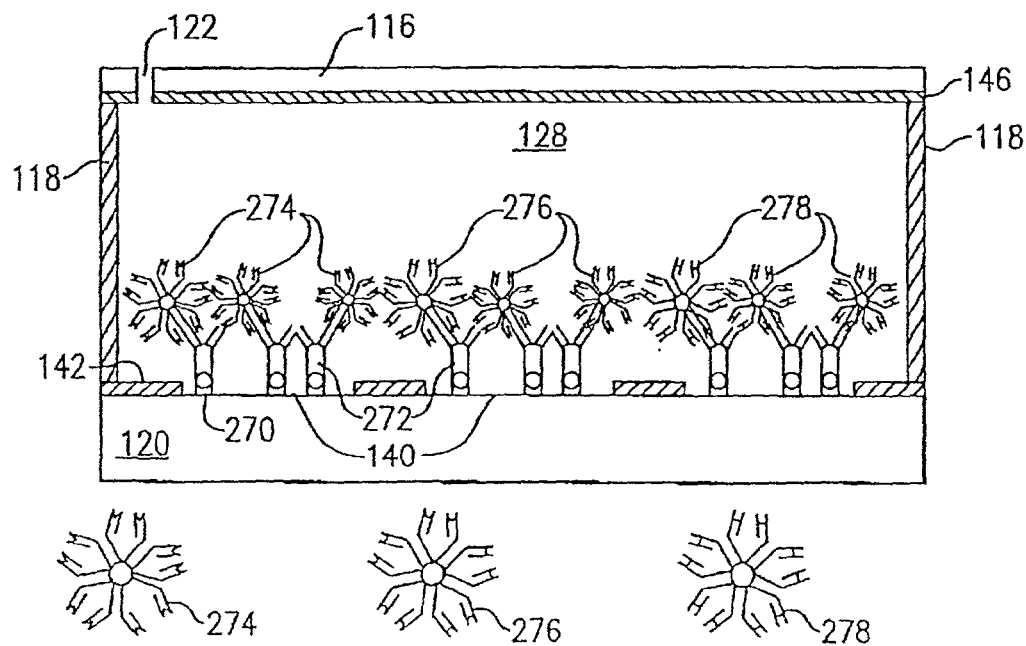
Figure 7F:
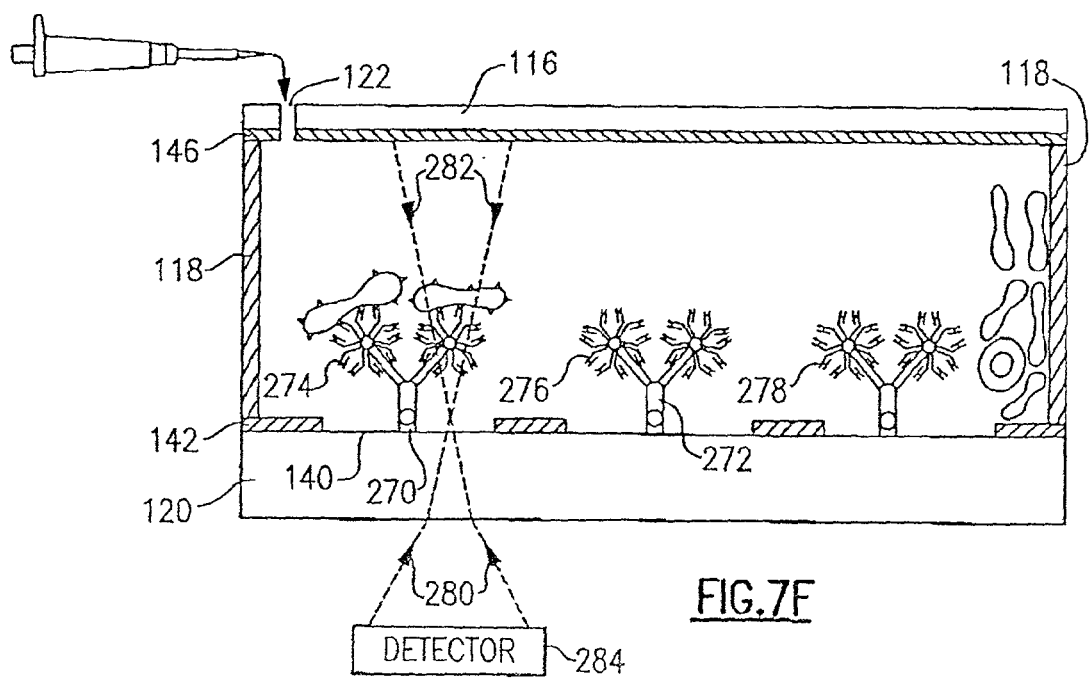

FIG. 7 shows a representation of the capture chemistry of one embodiment of the forward typing assay on a reflective zone disk. FIG. 7A shows the substrate 120 coated with reflective layer 142 and capture zones 140 where the reflective layer has been removed through lithography. FIG. 7B showts the layer of Streptavidin passively adsorbed to the capture zones 140. FIG. 7C shows the biotinylated first capture antibody 272 bound to the steptavidin 270 in the capture zones 140. FIG. 7D shows the second capture antibodies 274, 276 and 278 with different specificities bound to the biotinylated first capture antibody 272. FIG. 7E shows an assembled Bio-Disk with cap portion 116, reflective surface 146 and inlet port 122, adhesive member 118, channel 128 and capture chemistries 270, 272, 274 276 and 278 in the capture zones 140 on the substrate 120. FIG. 7F shows the specific cell capture based on the antigens expressed on the surface of the red blood cell. It also demonstrates the method of detection by focusing an incident beam of electromagnetic radiation 280 passing through a capture field 140 to strike a reflective layer, thereby producing a return beam of electromagnetic radiation 282 which is delivered to a detector system 284.

As used herein, the term "optical bio-disc" encompasses a disc, such as a compact disc (CD), having thereon a means

TABLE 1

| | Capture Layer Assembly and Variations | | | | | | | |
|---|---|---|---|---|---|---|---|---|
| Window | 1 | 2 | 3 | 4 | 5 | 6 | 7 | 8 |
| Optional Initial Layer | Streptavidin | Streptavidin | Streptavidin | Streptavidin | Streptavidin | Streptavidin | Streptavidin | Streptavidin |
| Optional 1$^{st}$ Capture Antibody* | Anti-IgX Antibody | Anti-IgX Antibody | Anti-IgX Antibody | Anti-IgX Antibody | Anti-IgX Antibody | Anti-IgX Antibody | Anti-IgX Antibody | Anti-IgX Antibody |
| 2$^{nd}$ Capture Antibody | Anti-A Antibody | Anti-B Antibody | Anti-D Antibody | Anti-C Antibody | Anti-c Antibody | Anti-E Antibody | Anti-e Antibody | Anti-C$^{W}$ Antibody |

*Indicates that the first capture antibody is biotinylated. IgX refers to any antibody inmmunoglobulin, e.g., IgG, IgM, etc.

In alternative embodiments, the bioactive surface can consist of five total layers in which the antibodies that comprise the bioactive capture layer are biotinylated and bind directly to the layer of streptavidin (or any variant thereof, the third layer). These and other variation of the cell for carrying out a biological assay, method or analysis. In addition, the disc is capable of being subjected to interrogation by a beam from a light source and data may be detected from the biological assay means. In addition, the disc may have information encoded on the disc itself which is available for detection by a disc drive assembly. The optical bio-disc is described in greater detail herein below.

As used herein, the term "chamber" encompasses any three-dimensional space defined by at least one material which is affixed to or part of an optical bio-disc. In one embodiment, the chamber is leak-proof so that a liquid sample may be loaded into the chamber and subjected to certain reaction conditions (such as antibody binding conditions) and to detection methods (such as beam interrogations). The chamber may be made of plastic, of metal, of glass or of any other material which is suitable for the biological assay for which the optical bio-disc is used. In one non-limiting example, the chamber may hold from about 4 µl to about 50 µl. In another example, the chamber is in fluid communication with a second chamber which can be utilized as a waste repository following the biological assay.

As used herein, an antibody which "specifically binds" means an antibody that binds to an epitope which comprises a peptide sequence or a carbohydrate moiety or a lipid moiety or a combination thereof. Such an antibody will not promiscuously bind to other molecules that do not have that specific epitope. Such a specifically binding antibody will not bind (or cross react) with other molecules or compounds lacking such an epitope.

The assay is performed within an optical bio-disc that includes a chamber (also, "flow chamber") having specific antibodies or other capture molecules attached to the solid phase associated with that chamber. In one non-limiting example of the invention, a method is described for the determination of the occurrence of a specific cell type (e.g., a specific type of red blood cell) expressing cell-specific surface antigens (e.g., A or B antigens) captured by specific antibodies affixed to the capture field(s).

An optical bio-disc may have multiple capture fields within one chamber. A grouping of several capture fields is termed a "bar code" because the data resulting from cells binding to certain capture fields resembles the dark and light striped pattern known as a bar code. In another example, also incorporated within such a bar code are defined negative control areas and positive control areas.

An optical bio-disc drive assembly is employed to rotate the disc, read and process any encoded information stored on the disc, and analyze the cell capture fields in the flow chamber of the bio-disc. The bio-disc drive is provided with a motor for rotating the bio-disc, a controller for controlling the rate of rotation of the disc, a processor for processing return signals from the disc, and analyzer for analyzing the processed signals. The rotation rate is variable and may be closely controlled both as to speed and time of rotation. The bio-disc may also be utilized to write information to the bio-disc either before, during or after the assay. The test material in the flow chamber and capture fields is interrogated by the read beam of the drive and analyzed by the analyzer. The bio-disc may include encoded information for controlling the rotation of the disc, providing processing information specific to the type of immunotyping assay to be conducted and for displaying the results on a monitor associated with the bio-drive.

The methods encompass evaluation tests in CD, CD-R or DVD formats. Variations or alternative versions thereof according to the present invention include a robust capture chemistry that is stabilized on the optical bio-disc. Unbound non-specific cells are spun off leaving behind specific target cells from the blood sample which are specifically bound to the capture field on the bio-disc. The read or interrogation beam of the drive detects the captured cells and generates images that can be analyzed.

Various aspects of the present invention are drawn to methods for typing blood. The surfaces of red blood cells contain large numbers of antigenic determinants that are classified into blood groups. These antigenic determinants represent red blood cell surface markers that consist of protein and/or carbohydrate moieties. In humans there are at least 23 blood type groups (*The Blood Group Antigen Factsbook* (Factsbooks Series) by Marion E. Reid (Editor) and Christine Lomas-Francis (Editor) (January 1997) Academic Press; ISBN: 0125859651). The ABO blood grouping is perhaps the most important, serving as the basis for the determination of transfusion compatibility. Another frequently relied upon red blood cell grouping is the Rhesus (Rh) blood grouping, which is an important test during pregnancy.

A variety of other blood typing systems are amenable to the methods of the invention. The most important of these include, but are not limited to, the MNSs System, the Lutheran System, the Kell System, the Lewis System, the Duffy System, and the Kidd System, the Fisher group, or another blood group. For a detailed discussion of blood transfusion technologies and the basis for blood group-typing, the following references are recommended:; *Transfusion Medicine* by Jeffrey McCullough (December 1997), McGraw-Hill Professional Publishing; ISBN: 0070451133; *Modern Blood Banking and Transfusion Practices* by Denise Harmening (Editor) (March 1999), F. A. Davis Co; ISBN: 080360419X; *Immunohematology: Principles and Practice* by Eva D. Quinley (Editor) (January 1998), Lippincott Williams & Wilkins Publishers; ISBN: 0397554699; and *The Principles and Practice of Blood Grouping* by Addine G. Erskine, ASIN: 0801615305.

Most blood typing tests are based on hemagglutination and involve mixing a blood sample with a panel of typing reagents that react with various surface antigens and cause the cells to agglutinate. The presence or absence of agglutination is an indication of a specific blood type. The invention described herein utilizes a cell-capture technology uniquely adapted to a bio-disc format. The biological assays of the invention are designed to detect cell agglutination or cell binding. In certain embodiments of the invention, the subject for blood typing is a mammal, e.g., a mouse or a human. In another example, the subject is a non-human mammal or a non-human primate.

In certain embodiments of the invention, methods are provided for ABO and/or Rh typing of blood. The specific antibodies and antigens relevant for the ABO blood typing system are presented in Table 2.

TABLE 2

The ABO Blood Type System

| Antigen | Antibody | Blood Group |
|---------|----------|-------------|
| A | Anti-B | A |
| B | Anti-A | B |
| A and B | None | AB |
| None | anti-A, anti-B | O |

Thus, individuals whose red blood cells carry the A antigen have antibody in their system directed against the B antigen, and individuals whose red blood cells carry the B antigen have antibody in their system directed against the A antigen. Individuals with both A and B antigens on their red blood cells produce no antibody directed against these antigens, and individuals with neither antigen present on their red blood cells have antibodies directed against both antigens in their system.

In Rh blood typing system, there are three genes making up Rhesus antigens: C, D, and E, all found on chromosome 1. There are two possible alleles at each locus: c or C; D; and e or E. If an individual's Rh genotype contains at least one of the C, D, E antigens, they are Rhesus positive. Only individuals with the genotype cde/cde (rr) are Rhesus negative.

Figure 8:
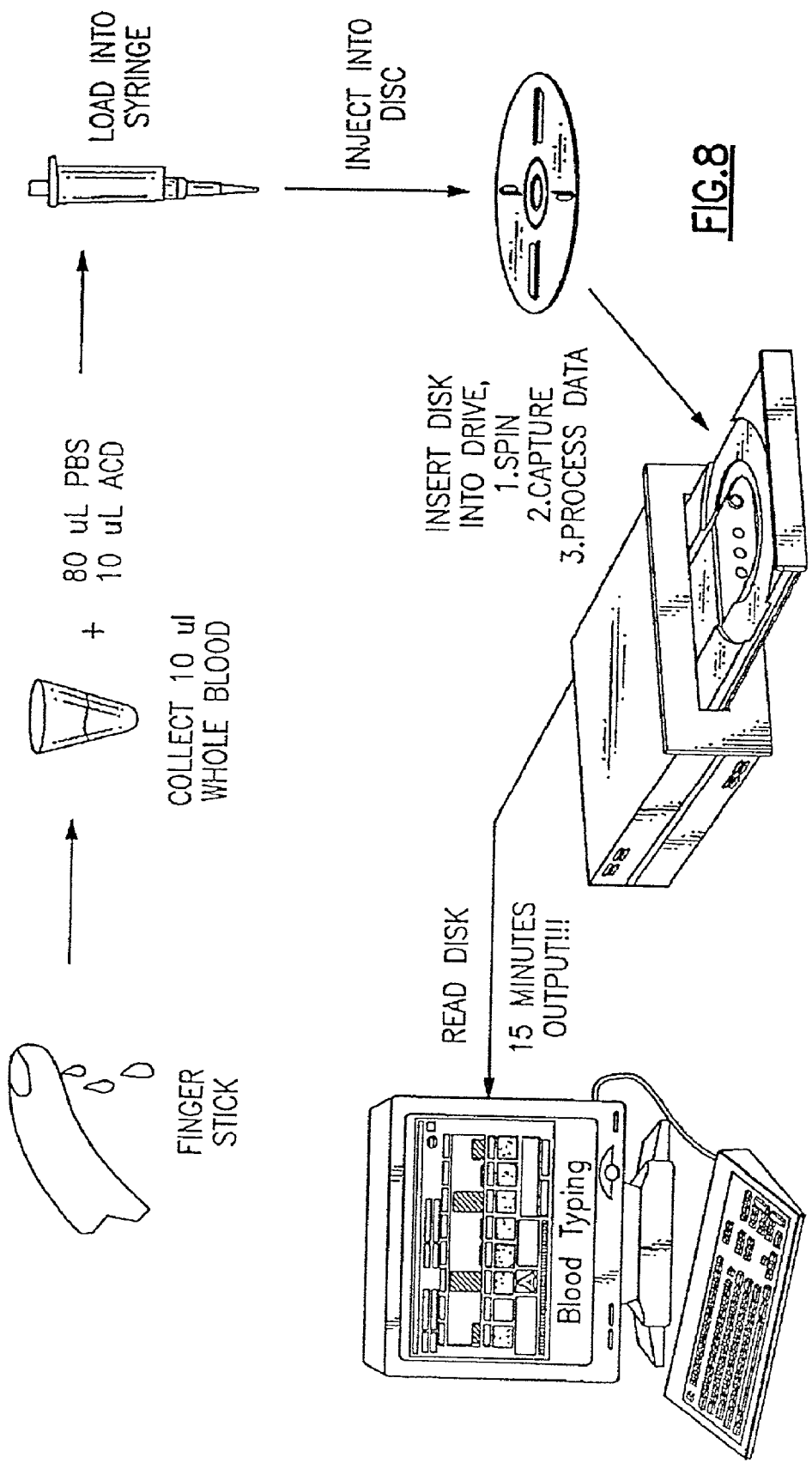
FIG. 8 is a pictorial flow diagram presenting one example of a forward ABO/Rh blood typing method of the invention.
Figure 9:
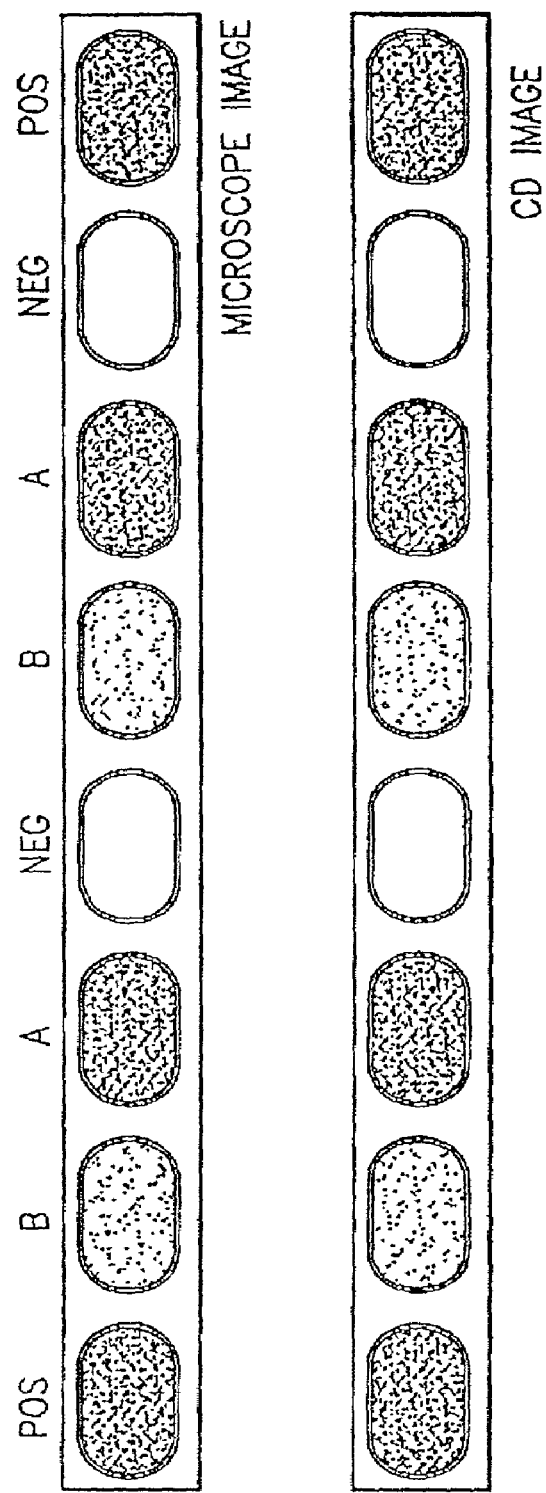
FIG. 9 is a plan view illustrating data output in the form of a bar code.

Referring to FIG. 8, the invention provides a system for blood typing or the detection of antibodies directed against a particular blood type. The system includes methods for the isolation and processing of whole blood, introduction of the sample into an optical bio-disc having at least one chamber with a target zone 170 and capture fields contained therein, an optical disc reader, and a system for the data processing and a display for data presentation.

Figure 10:
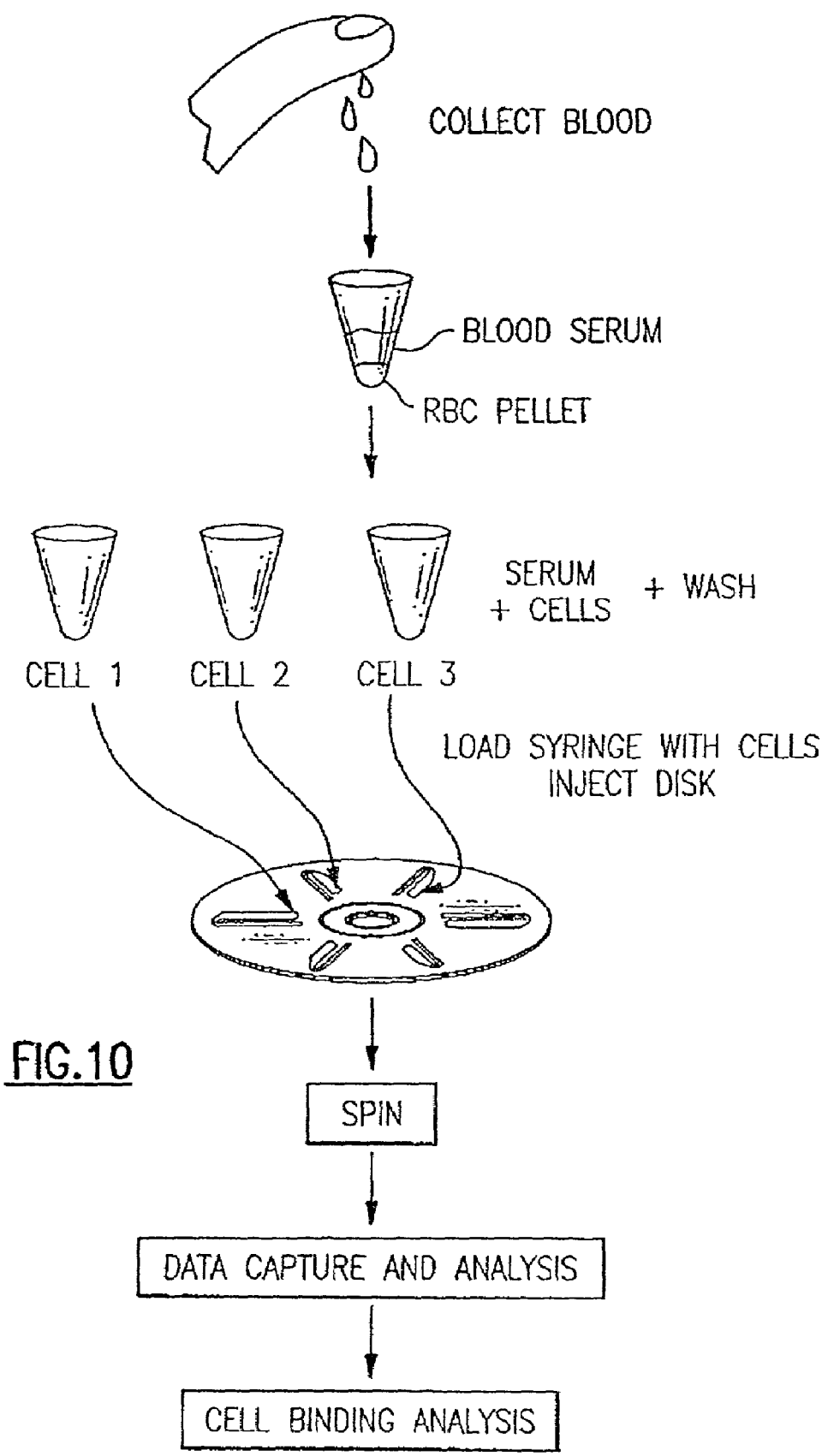
FIG. 10 is a pictorial flow diagram demonstrating the method of antibody typing for blood groups other than the ABO/Rh bloods with sample preparation off-disc and sample analysis on disc.
Figure 11:
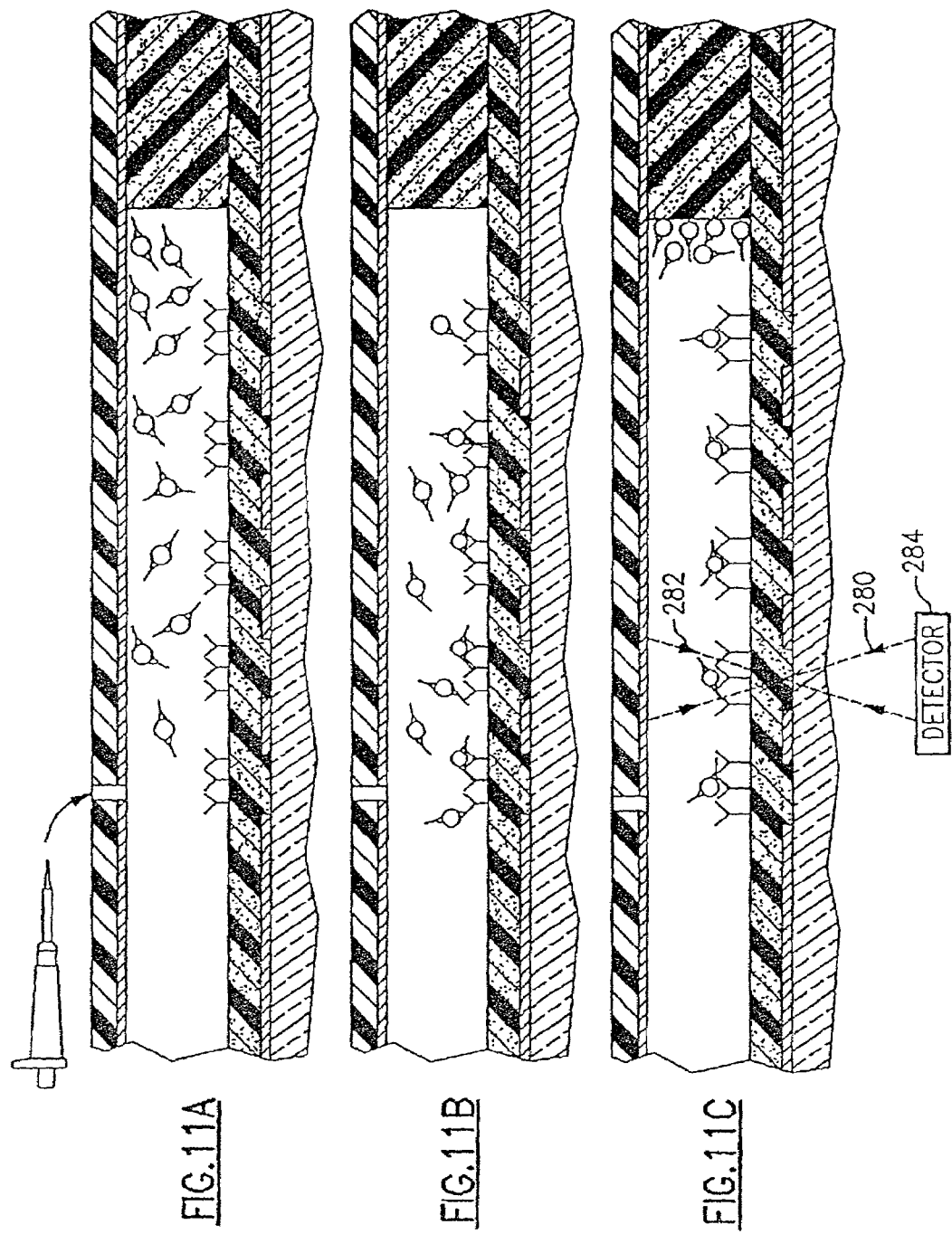
FIGS. 11A–C is schematic presenting a series of side views that show red blood cells bound by antibodies (11A), red blood cells with antibody bound in contact with the capture field (11B), and red blood cells bound by antibodies being captured by the capture field (11C).
Figure 12:
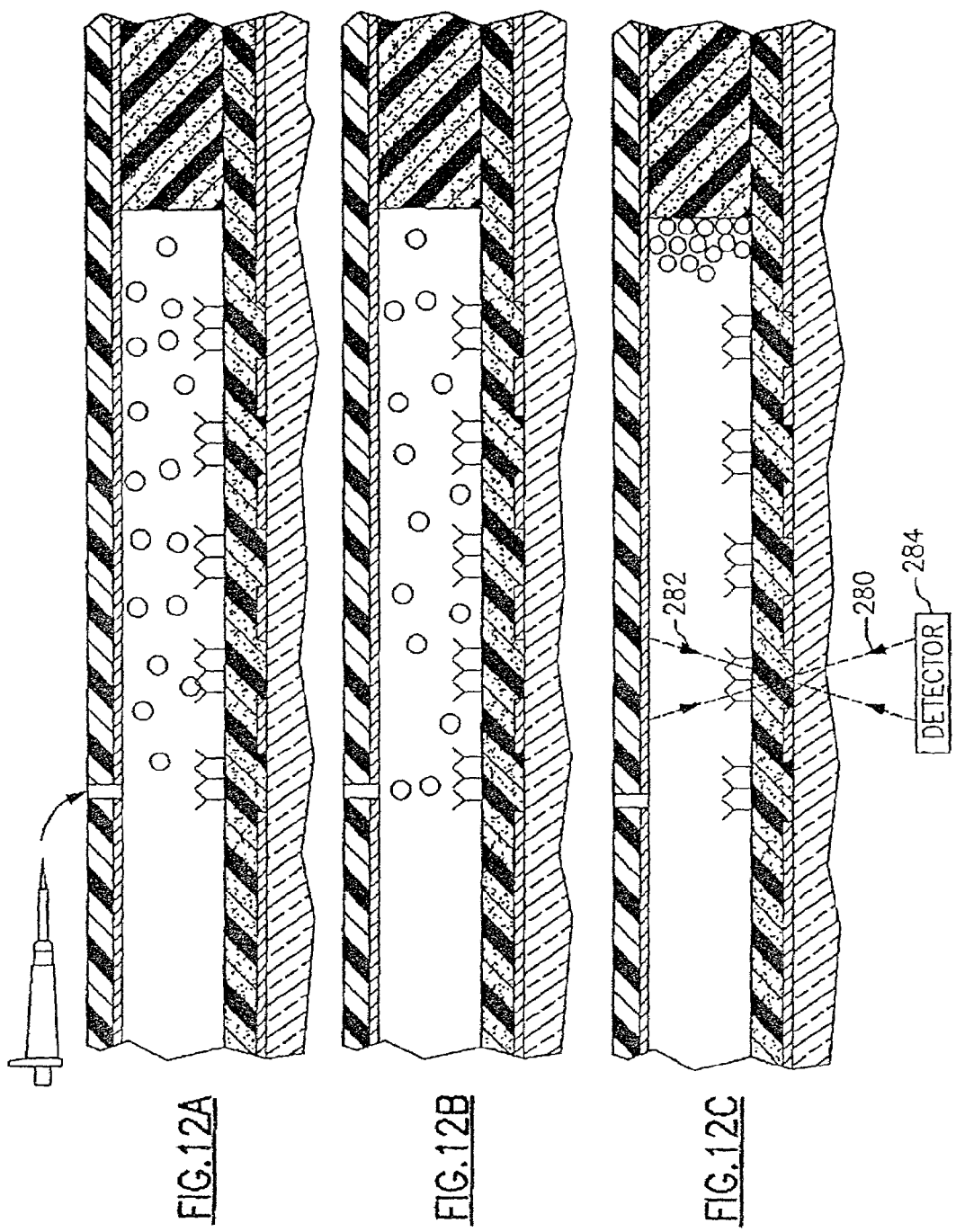
FIGS. 12A–C is schematic presenting a series of side views that show red blood cells bound not recognized by antibodies (12A), red blood cells without antibodies bound thereto in contact with the capture field (12B), and red blood cells without antibodies bound thereto not being captured by the capture field (12C).

Bio-assay methods of the invention can be conveniently designed into a "bar code" format for sample testing and data presentation. By way of non-limiting example, this particular embodiment for blood typing is illustrated in FIGS. 10. In this embodiment, one optical bio-disc would contain thereon several capture fields, each of which has affixed thereto a capture agent, e.g., antibody, which is specific for a particular determinant on the surface of a red blood cell. A direct benefit of this type of approach is that the characteristic pattern of a particular blood-type would be predetermined as a barcode readout. Therefore, the subsequent analysis of blood samples from subjects would then be compared to the known barcode result in order to determine the blood-type of that subject immediately. For example, one strip of capture fields on a bio-disc includes separate capture fields which are arranged in a row and are in fluid communication with one another and which have affixed thereto capture antibodies specific for the red blood cell A or B antigens. The optical bio-disc and disc reader assembly would allow a person to carry out blood typing analysis in the field (that is, not in a clinical setting) expeditiously.

Figure 13:
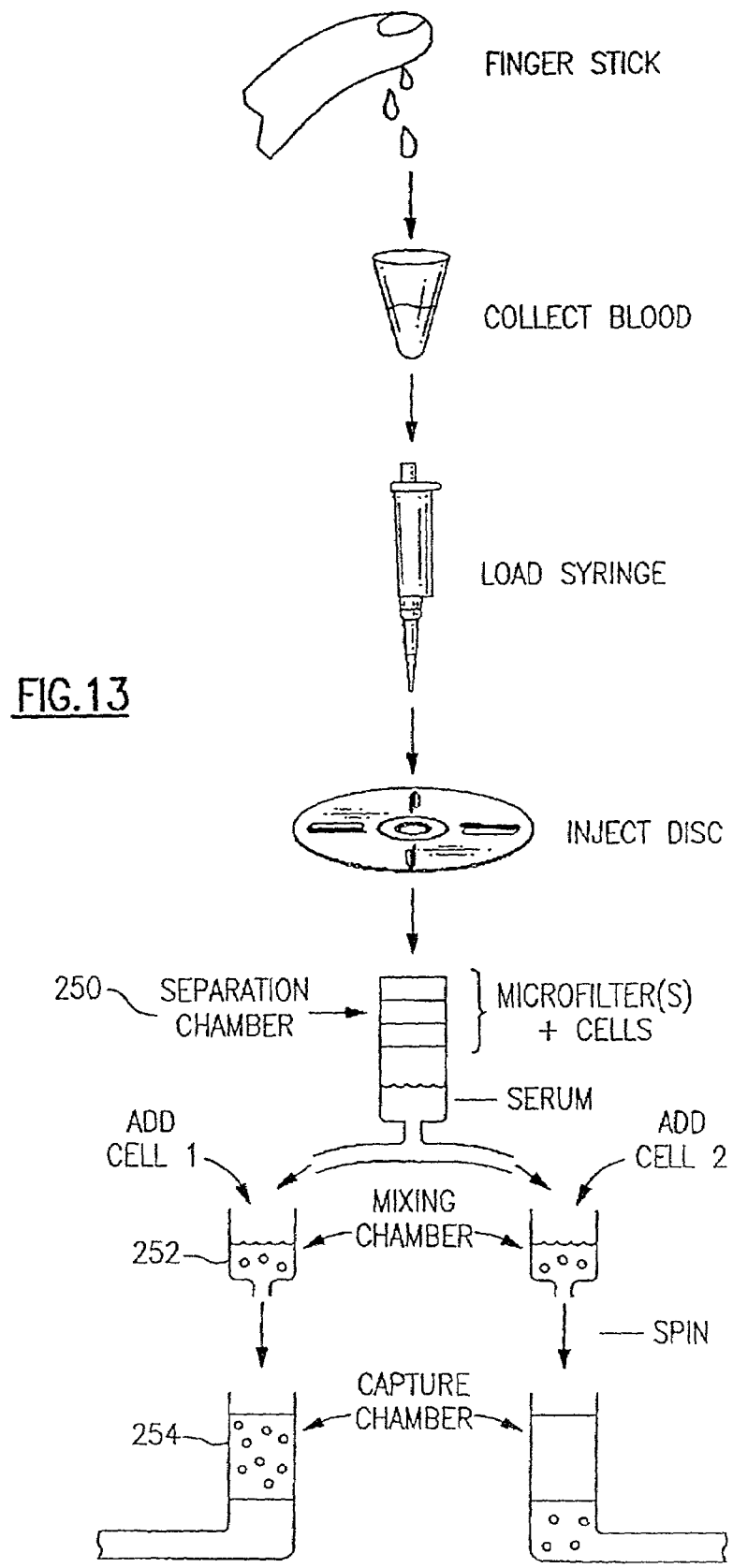
FIG. 13 is a pictorial flow diagram presenting the method of antibody typing wherein sample preparation and processing are all done on the optical bio-disc. The schematic of the left capture chamber presents cells bound to the capture field as previously presented in FIG. 11C, whereas the schematic of the right capture chamber presents cells without antibody bound thereto not being bound to the capture field as previously presented in FIG. 12C.

In one aspect, the invention provides a methods for antibody typing a blood sample, i.e., assaying a patients serum for the occurrence of antibodies directed to an antigen of a blood group other than that of the ABO system. In one embodiment, the invention provides a method for antibody typing wherein the sample undergoes processing prior to being loaded onto a bio-disc (FIG. 10 and 11A–C, 12A–C). In another embodiment, the invention provides a method for antibody typing wherein the sample is loaded onto a bio-disc without significant processing (FIG. 13). Cells of a known blood group phenotype other than that of the ABO system, e.g., Kell, Duffy Kidd, etc., are available commercially for testing purposes, (Immucor, Inc. Norcross, GA, PANO-SCREEN®).

Referring to FIG. 10, in the first embodiment of antibody typing, whole blood is first separated from serum prior to utilizing the serum in the bio-disc blood grouping assay. Whole blood can be separated into serum and cells by light centrifugation. The serum, which contains a patient's antibodies, is then mixed with one or more O type ABO cells having a known phenotype for a blood group type other than that of ABO. The sample is incubated for a period of time, e.g., about fifteen to thirty minutes, at 37° C. to allow the patients antibodies to interact with these cells. After incubation, the cells are washed several times and loaded into one or more chambers in the bio-disc. If antibodies of the appropriate specificity are found in the patient's serum, the red blood cells will have the antibodies bound thereto. These antibody-bound cells can then be captured on a capture field by an appropriate capture agent, e.g., an anti-human IgG. After a brief spin of the disc (e.g., 400 rpm to 4000 rpm) to remove unbound cells, the capture field is examined for the occurrence of cells. The capture field can then be examined by the optical reader to determine whether cells being tested are present in the capture field, and thereby determine the antibody status of the individual.

Figure 14:
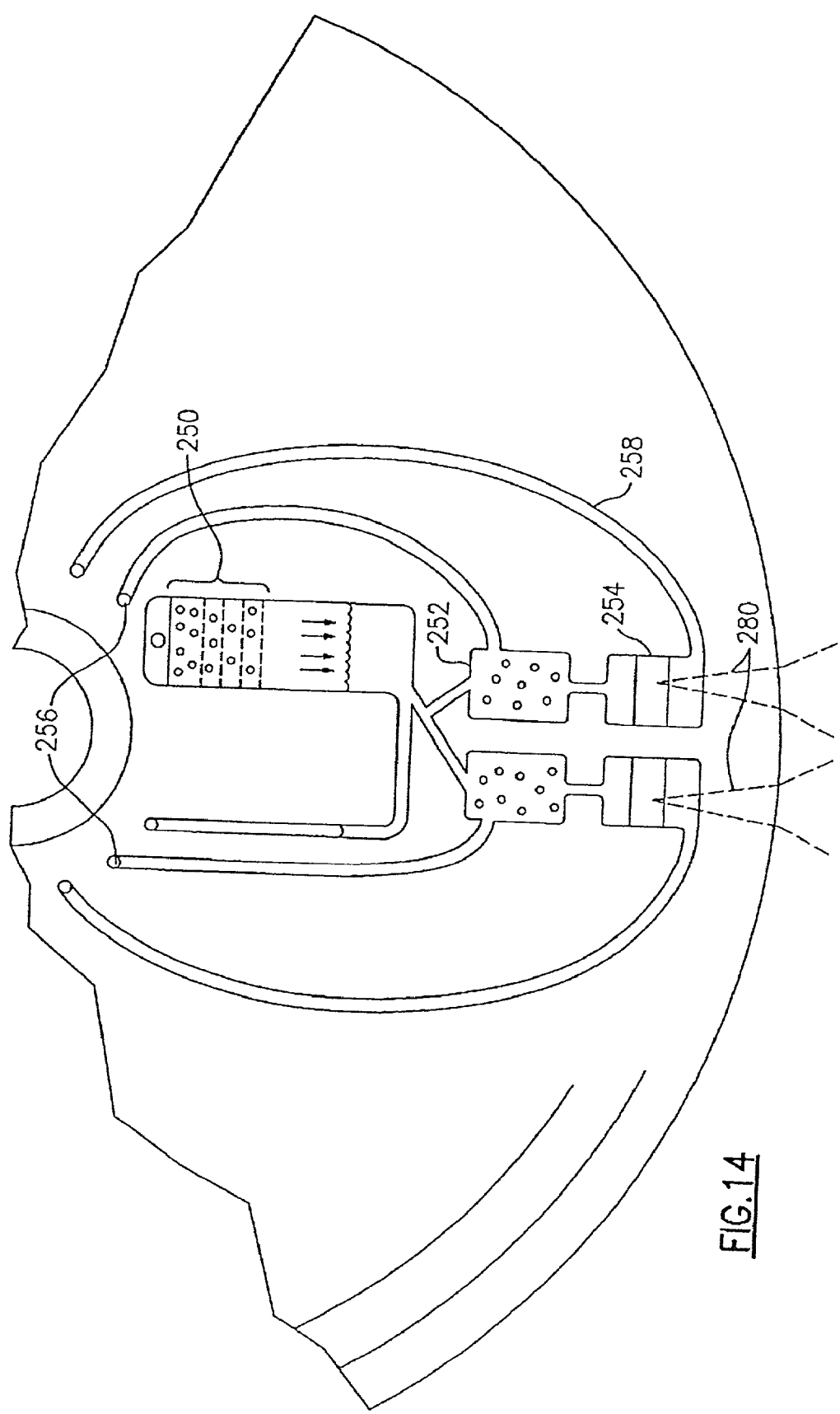
FIG. 14 is a plan view schematic representing one example of a microfluidic circuit containing two inlet ports, a separation chamber, two mixing chambers, two capture chambers, and the incident beam of electromagnetic radiation directed at the capture chamber.

In the second embodiment of antibody typing, whole blood, or a diluted sample thereof, is loaded directly onto the bio-disc into a microfluidic circuit (FIG. 14). The method provides for the separation of blood cells and serum by passage through a separation chamber 250 in the optical bio-disc. Separation of the fluid and cellular components of whole blood is effected by spinning the disc at a first speed, thereby moving the sample through at least one microfilter designed to separate red blood cells, white blood cells and platelets from the serum. Serum is then moved to at least one mixing chamber 252 by spinning the disc at a second speed, which is higher than the first speed. Cells of a known blood group phenotype are then added through a separate entry port 256 into at least one mixing chamber of the bio-disc.

With various aspects of the invention, the microfluidic circuit has inlet ports 256 for the addition of cells of a known blood group phenotype to the mixing chamber(s). In other various aspects of the invention, the inlet port(s) 256 are not necessary, since the mixing chamber has been preloaded with a microparticle coated with a specific antigen of a red blood cell blood type group, e.g., A antigen or B antigen. Such particles may be conveniently prepared by purifying the red blood cell antigen, e.g., through recombinant gene expression and subsequent biochemical isolation, absorbing it onto the particles. These particles may then be loaded into the mixing chamber during construction of the bio-disc, e.g., in freeze-dried form. A bio-disc of this construction would be particularly useful in countries and areas where access to red blood cells of a known blood type phenotype is difficult.

Mixing of the serum and cells is accomplished by spinning the disc at least once one-half a rotation counter clockwise and then clockwise one-half a rotation. The samples are then allowed to incubate in the mixing chamber for a sufficient time to allow antibody-antigen interaction. The cells are then moved to a capture chamber 254 with a capture field by spinning the disc at a third speed, which is higher than the second speed. The cells are allowed to interact with the capture field, which has bound to it anti-human IgG, for a sufficient time to allow antibody-antigen interaction. The disc is then spun again to remove unbound cells (e.g., 400 rpm–4000 rpm) Data is then collected from the capture fields to determine if cells are bound to the capture field. The occurrence of cells in a capture field indicates that the individual's serum has antibodies directed to an antigen on the surface of the particular red blood cell blood type phenotype being tested.

In one aspect, the invention provides a method of antibody typing a blood sample on an optical bio-disc. With this method, blood may be conveniently isolated by finger-stick, diluted and loaded into the bio-disc for processing. Ideally, multiple capture fields are exposed to the sample being tested. The multiple capture fields serve the purpose of providing separate test areas in a target zone 170, each bound by a unique capture agent. By way of non-limiting example, unique capture agents in a test designed for the ABO blood system would include anti-A antibody and anti-B antibody, each loaded onto separate capture fields on the disc. Antibodies with the appropriate specificity for antigens of different blood groupings are available commercially (e.g., anti-A and anti-B antibodies may be obtained from Fisher Scientific, Los Angles, Calif., Catalogue Nos. 23287247 and 23287248, respectively).

Positive and negative controls for the test would include a positive control capture field in which the capture agent is a molecule that binds all cells, e.g., a lectin isolated from *Lycopersicon esculentum* that binds β-D-glucosamine oligomers (Sigma Aldrich Chemical, Catalogue No. L-0651), and a negative control capture field having no capture agent bound thereto, Various embodiments of this method of the invention may be similarly designed for the purpose of blood typing according to any other blood typing system, e.g., for testing the Rh system blood group, the MNSs system blood group, the Lutheran system blood group, the Kell system blood group, the Lewis system blood group, the Duffy system blood group, the Kidd system blood group, the Fisher system blood group, or any other blood group. As will be understood by those in the art, one or more blood type systems may be simultaneously tested on a single bio-disc.

The remaining blood groups may complicate a blood typing but are not as important. In an individual, antibodies to the antigens not expressed on red blood cells are non-red-cell stimulated (or naturally occurring), due to the similarity between the blood group antigens structure and environmental agents. The antibodies may be of the IgM, IgA or IgG class. The IgM antibodies can cause direct agglutination when mixed with cells bearing the antigen the antibody is directed against. When an individual is exposed to red cells that are incompatible with his or hers, either through a transfusion or through pregnancy, the antibodies which are produced are predominately of the IgG class. The IgG antibodies can cross the placenta and cause hemolytic disease of the newborn in subsequent pregnancies.

As stated above, the ABO and Rh blood groups are the most important groups in transfusion medicine. Naturally occurring antibodies to the ABO and Rh antigens are of the IgM class. Antibodies to the ABO and Rh antigens are readily available and direct agglutination tests can be performed on red blood cell samples. In the system of the present invention, for forward typing assays, agglutination of the red cells is not the test; the test in this instance is cell capture based on antigen-antibody interactions. The interaction is specific and accurate and indicates which antigens are present on the red blood cell surface. For reverse typing of the ABO antibodies, agglutination of cells captured on the optical disk is looked for and analyzed by software algorithm(s).

Figure 18:
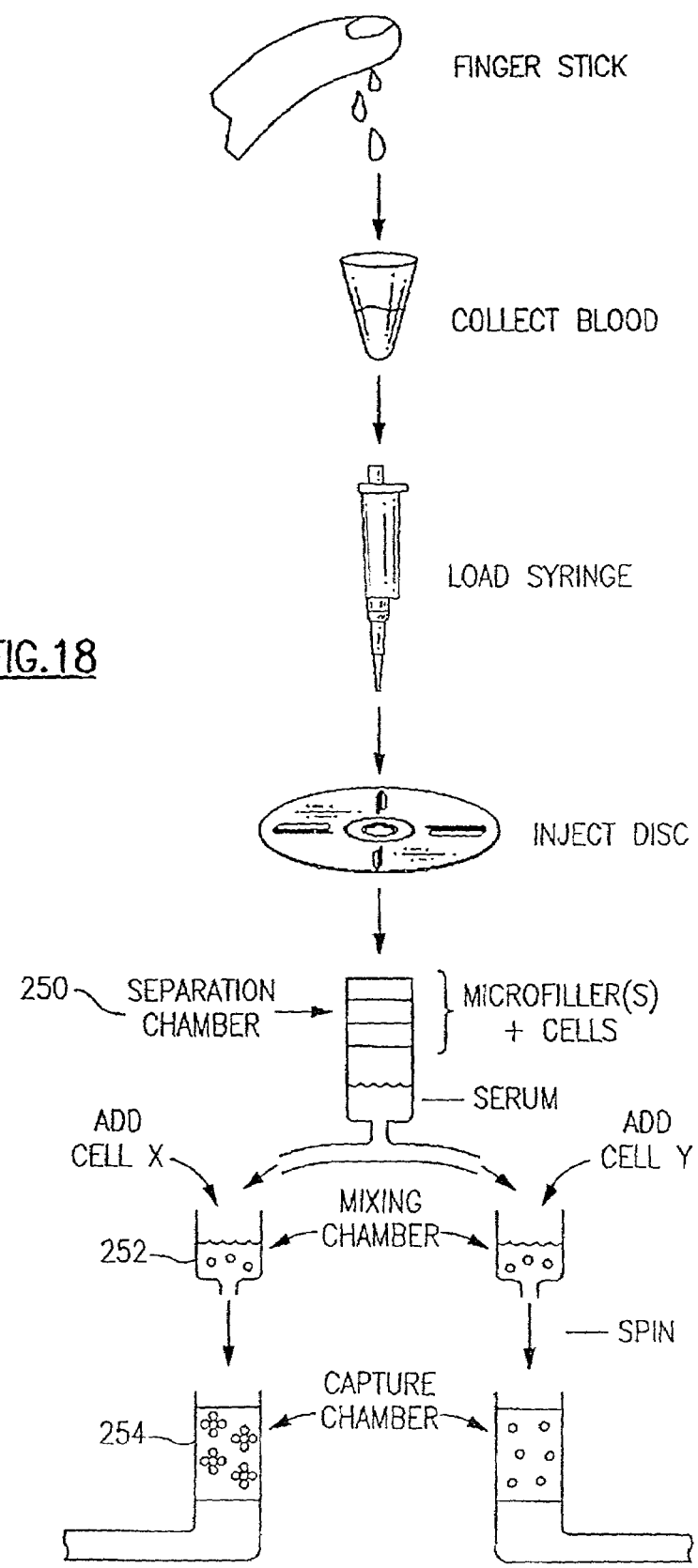
FIG. 18 is a pictorial flow diagram presenting the method of reverse ABO/Rh typing wherein sample preparation and processing are all done on the optical bio-disc. The schematic of the left capture chamber presents cells bound to the capture field as previously presented in FIG. 16C, whereas the schematic of the right capture chamber presents cells bound to the capture chamber as previously presented in FIG. 17C.

The invention provides a methods for detecting specific antibodies to an ABO/Rh blood group antigen, e.g., assaying a patients serum for the occurrence of anti-A or anti-B antibodies. In one embodiment, the invention provides a method for reverse typing wherein the sample undergoes processing prior to being loaded onto a bio-disc (FIG. 15 and 16A–C and 17A–C). In another embodiment, the invention provides a method for reverse typing wherein the sample is loaded onto a bio-disc without significant processing (FIG. 18).

Figure 15:
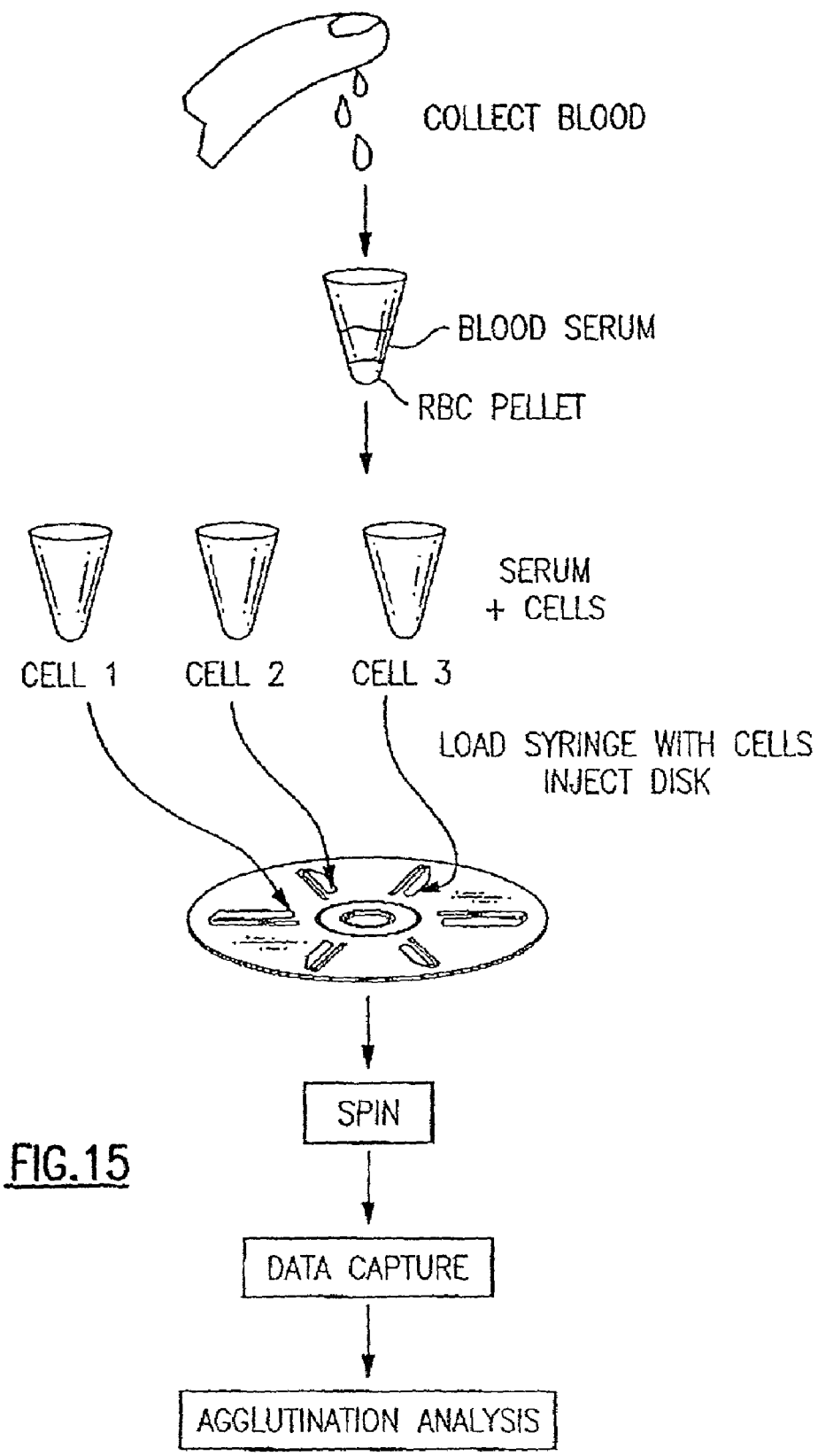
FIG. 15 is a pictorial flow diagram illustrating a method of reverse typing for the ABO/Rh blood groups with sample preparation off-disc and sample analysis on disc.
Figures 16A, 16B, 16C:
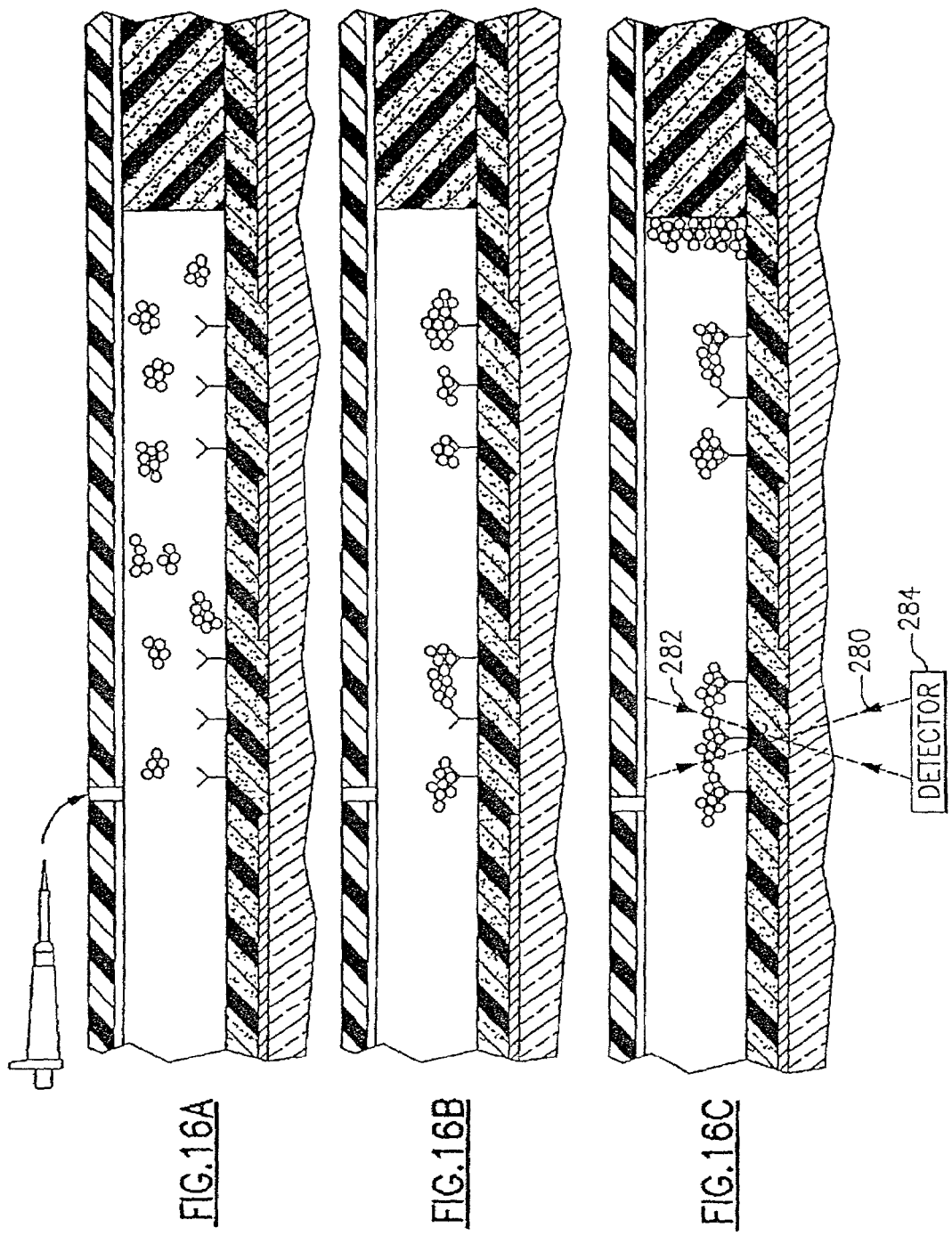
FIG. 16A shows red blood cells agglutinated after contact with antibodies direct to an ABO/Rh group antibody.
FIG. 16B shows the same red blood cells interacting the capture field.
FIG. 16C shows the capture of antibody-bound, agglutinated red blood cells by a lectin or antibody.

Referring to FIG. 15, in the first embodiment of reverse typing, whole blood is first separated from serum prior to utilizing the serum in the bio-disc blood grouping assay. Whole blood can be separated into serum and cells by light centrifugation. The serum, which contains a patient's antibodies, is then mixed with one or more cells having an ABO cell phenotype. The sample is incubated for a period of time, e.g., about one to five minutes, at room temperature to allow the patient's antibodies to interact with these cells. After incubation, if an anti-human antibody is used as the capture agent, the cells are washed several times and loaded into one or more chambers in the bio-disc; if a lectin capture agent is used, washing is unnecessary.

If antibodies of the appropriate specificity are found in the patient's serum, the red blood cells will be agglutinated as a result of the antibodies bound thereto. These agglutinated cells can then be captured on a capture field by an appropriate capture agent, e.g., a lectin that binds all cells. After a brief spin of the disc, e.g., 400 rpm to 4000 rpm, to remove unbound cells, the capture field is examined for the occurrence of agglutinated cells. The capture field can then be examined by the optical reader to determine whether cells being tested are agglutinated, and thereby determine that antibodies to an ABO/Rh blood group antigen were present in the individual's blood.

In the second embodiment of reverse typing, whole blood, or a diluted sample thereof, is loaded directly onto the bio-disc into a microfluidic circuit (FIG. 14). The method provides for the separation of blood cells and serum by passage through a separation chamber 250 in the optical bio-disc. Separation of the fluid and cellular components of whole blood is effected by spinning the disc at a first speed, moving the sample through at least one microfilter designed to separate red blood cells, white blood cells and platelets from the serum. Serum is then moved to at least one mixing chamber 252 by spinning the disc at a second speed, which is higher than the first speed. Cells of a specific ABO group phenotype are then added through a separate port entry into at least one mixing chamber. Mixing of the serum and cells is accomplished by spinning the disc at least once one-half a rotation counter clockwise and then clockwise one-half a rotation. The samples are then allowed to incubate in the mixing chamber for a sufficient time to allow antibody-antigen interaction. The cells are then moved to a capture chamber 254 with a capture field by spinning the disc at a third speed, which is higher than the second speed. The cells are allowed to interact with the capture field which has bound to it anti-human immunoglobulin or another capture agent for a sufficient time to allow capture agent interaction with the cells. The disc is then spun again to remove unbound cells, e.g., 400 rpm to 4000 rpm. Data is then collected from the capture fields to determine if cells bound thereto are agglutinated. The occurrence of agglutinated cells in a capture field indicates that the individual's serum has antibodies directed to an antigen on the surface of the particular red blood cell blood type phenotype being tested.

In a seventh aspect, the invention provides an optical-bio disc for performing a blood-typing assay, the disc comprising: a substrate; a separation chamber associated with the substrate, the separation chamber including an inlet port; filter means associated with the separation chamber; a first mixing chamber in fluid communication with the separation chamber, the first mixing chamber including an inlet port; a second mixing chamber in fluid communication with the separation chamber, the second mixing chamber including an inlet port; a first detection chamber in fluid communication with the first mixing chamber, the first detection chamber including a capture zone; and a second detection chamber in fluid communication with the second mixing chamber, the second detection chamber including a capture zone.

In certain embodiments of this aspect, when a sample of blood is directed into the separation chamber through the inlet port and the disc is rotated at a first speed, the filter means separates white blood cells, red blood cells, and platelets from the blood sample to provide a sample of serum. In a further embodiment, when the disc is rotated at a second speed, the sample of serum is directed into the first and second mixing chambers. In another embodiment, the inlet port of the first mixing chamber is employed to direct cells of a first type into the first mixing chamber, and the inlet port of the second mixing chamber is employed to direct cells of a second type into the second mixing chamber. In other certain embodiments, when the disc is rotated at a third speed, a mixture of serum and cells of the first type is directed into the first detection chamber, and a mixture of serum and cells of the second type is directed into the second detection chamber.

Certain embodiments of the seventh aspect provide for disc rotation in a predetermined manner to mix the cells of the first type with serum in the first mixing chamber, and mix the cells of the second type with serum in the second mixing chamber. In certain embodiments, the predetermined manner of rotating the disc includes alternately rotating the disc in one direction and then an opposite direction to thereby create an agitation action to promote mixing of serum and cells.

In certain embodiments of the seventh aspect, the capture zone in the first detection chamber includes a first type of capture agent implemented to capture specific cells having any affinity therefor. In other certain embodiments, the capture zone in the second detection chamber includes a second type of capture agent implemented to capture specific cells having any affinity therefor.

In certain embodiments of the seventh aspect, an incident beam of radiant energy is directed into the first detection chamber to determine whether any cells were captured by the first type of capture agent. In other embodiments, an incident beam of radiant energy is directed into the second detection chamber to determine whether any cells were captured by the second type of capture agent.

In certain embodiments of the seventh aspect, the first type of capture agent is an anti-human immunoglobulin having an affinity for an antibody bound to the cells or a non-cell specific molecule that binds a molecule on the surface of all red blood cells. In certain embodiments of the seventh aspect, the second type of capture agent is an anti-human immunoglobulin having an affinity for an antibody bound to the cells or a non-cell specific molecule that binds a molecule on the surface of all red blood cells.

In certain embodiments of the seventh aspect, the separation chamber, the first and second mixing chambers, and the first and second detection chambers are formed in the substrate. In other certain embodiments of the seventh aspect, the separation chamber, the first and second mixing chambers, and the first and second detection chambers are formed in a cap bonded to the substrate. In yet other certain embodiments of the seventh aspect, the separation chamber, the first and second mixing chambers, and the first and second detection chambers are formed in a channel layer bonded between a cap portion and the substrate. In certain embodiments of the seventh aspect, the separation chamber, the first and second mixing chambers, and the first and second detection chambers are partially formed in a cap portion and partially formed in the substrate, the cap portion and the substrate being bonded together in register to thereby fully form the chambers.

In certain embodiments of the seventh aspect, the optical bio-disc further includes information encoded in an information layer readable by a disc drive. In certain embodiments thereof, the encoded information is used to rotate the disc in a prescribed manner. In certain embodiments of the seventh aspect, the information layer is reflective. In other embodiments, the information layer is semi-reflective.

In an eighth aspect, the invention provides a method for manufacturing a disc comprising: providing over a substrate of the disc an encoded informational layer; forming target areas; providing a capture layer in the target areas; attaching at least one capture agen. In certain embodiments, the encoded informational layer is a reflective layer, annd the target areas are regions etched from the reflective layer. In certain embodiments, the encoded informational layer is a partially reflective and partially transmissive layer, and the target areas are regions adjacent the informational layer.

EXAMPLES

Example 1

Bio-Disc and Capture Layer Preparation

In one embodiment, the tracking of the bio-disc of the present invention is a forward Wobble Set FDL21:13707 or FDL21:1270 coating with 300 nm of gold. On this reflective disk, oval data windows of size 2×1 mm are etched out by Lithography. "U" shaped channels are used to create chambers that are 25 um in height. It takes about 7 uls of sample to fill the entire chamber including the inlet and outlet ports. A 8-window/4-channel format to be preferentially used. In the preferred embodiment of the invention a semi-reflective transmissive disc (FDL 20/21:00708) is used which allows the entire surface of a transmissive disk may be used for capture zones, without the use of lithography to form data windows. Fraylock "U" shaped adhesive DBL 201 Rev C 3M94661 or straight channels are used to create the chambers. The cover disc utilized is a gold disk, fully reflective with 48 sample inlets with a diameter of 0.040 inches location equidistant at radius 26 mm.

Several chemical layers are applied sequentially to the solid substrate first layer. This first layer may be a polycarbonate layer or a metallized polycarbonate layer in a optical disc such as a CD, CD-ROM, DVD or DVD-ROM. Prior to subsequent treatment, the first layer is cleaned with isopropanol. The second layer consists of either polystyrene or polycarbonate. This layer may be formed by injection molding of bulk plastic or spin or spray coating of the plastic in a volatile solvent on a solid substrate.

The primary capture layer, the third layer, is formed by absorption of the protein streptavidin (Sigma, St. Louis, Mo., Catalogue No. S-4762) (or any variant thereof) on the second layer. The adsorption process is accomplished by exposure of the second layer to a first solution (1 mg/ml solution of streptavidin (or any variant thereof) at neutral pH (+/−0.5 pH) in either phosphate (sodium or potassium) or Tris buffer, ionic strength (varied by addition of NaCl, KCl or MgCl2) between 50 and 200 mM). Exposure times may range between 30 seconds and 12 hours. After exposure of the second layer to the first solution, the excess streptavidin (or any variant thereof) is washed away with water.

The secondary capture layer, the fourth layer, consists of biotin-labeled antibody (the first capture antibody) that recognize and bond to other antibodies from a certain animal source (e.g., mouse or human) (e.g., biotinylated anti-mouse IgG (raised in sheep), Vector Laboratories, lot #L0602, Catalog #BA-9200). A solution of the first capture antibody (the second solution) is exposed to the third layer for between 10 minutes and 3 hours. The second solution comprises a 1 mg/ml solution of the first capture antibody at neutral pH (+/−0.5 pH) in either phosphate (sodium or potassium) or Tris buffer, ionic strength (varied by addition of NaCl, KCl or MgCl2) between 50 and 200 mM. The biotin moiety on the surface of the first capture antibody is bound by the streptavidin (or any variant thereof) which comprises the third layer. After exposure of this layer to the second solution, the excess first capture antibody is washed away with water.

The bioactive capture layer, the fifth layer, consists of the second capture antibody, which recognizes and binds to a specific type of biological cell based on some antigen on the surface of that cell. The animal source of the second capture antibody must match the specificity of the first capture antibody. A solution of the second capture antibody is exposed to the fourth layer for between 10 minutes and 3 hours. This third solution comprises a 1 mg/ml solution of the second capture antibody at neutral pH (+/−0.5 pH) in either phosphate (sodium or potassium) or Tris buffer, ionic strength (varied by addition of NaCl, KCl or MgCl2) between 50 and 200 mM. After exposure of the fourth layer to the third solution, excess second capture antibody is washed away with a buffer similar to that described above.

Since blood is analyzed, the discs of the invention are leak checked to make certain that none of the chambers leak during spinning of the disc with the sample in situ. Each channel is filled with a blocking agent. Blocking is done for least 1 hour. The discs are then spun at 5000 rpm for 5 minutes and examined. After checking for leaks and removing the blocking solution, the disc is placed in a vacuum chamber for 2–48 hours. After vacuum treatment, discs are placed in a vacuum pouch and stored at 2–8° C. until use.

Additionally, the disc can be heat or ultrasonically bonded to make certain no fluid escapes from the chamber.

Example 2

Forward Blood Typing Assay On Bio-Disc

In the example to follow, the forward blood typing assay is conducted on a bio-disc comprising: (1) gold reflective base disc, treated with photo-lithography to remove the gold in specific capture zones, with appropriate chemistry placed over the capture zones, (2) 25 um thick channel layer, and (3) gold reflective cover disc, assembled into a functional bio-disk.

10 ul of whole blood from a finger stick is diluted in 90 ul of phosphate buffered saline/anticoagulatant to make a 10% RBC solution. 7 ul of this is injected into the functional bio-disk and the inlet and vent ports are sealed. After a five-minute room temperature incubation, the disk is placed into the drive. The automated event counting software developed in-house centrifuges the disk, causing the non-specifically captured cells to be removed from the capture zones. The disk is scanned with the standard 780 nm laser of the optical drive using the bottom detector and the software registers the number of events in each capture zone. The program algorithm determines which capture zones had a positive capture and assigns an ABO and Rh phenotype to the blood sample. The entire process takes about 10 minutes from insertion of disk into the drive and receiving the forward blood typing.

Figure 19:
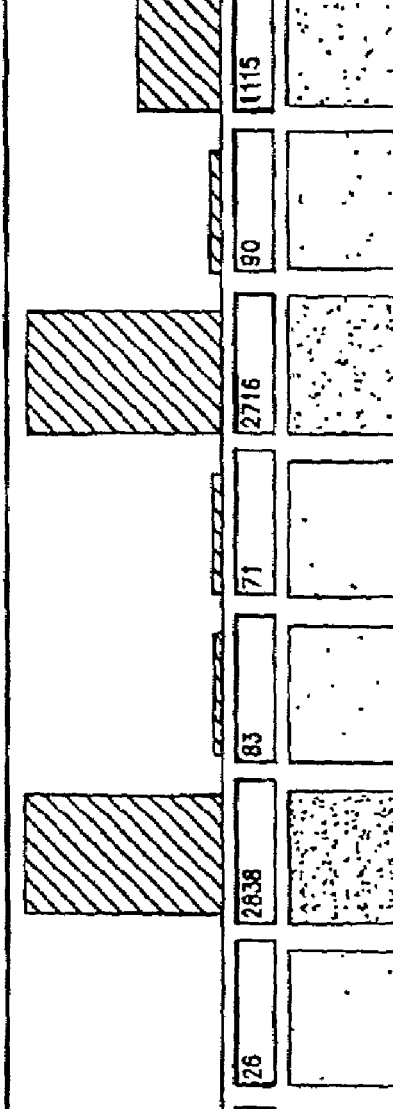
FIG. 19 is a pictorial of a computer monitor screen shot presenting an output of an ABO blood typing test.

Results are presented in FIG. 19, which is a representation of a graphical output for ABO blood typing.

Example 3

Antibody Typing Assay On Bio-Disc (Sample Preparation Off-Disc)

In the example to follow, the reverse blood typing assay is conducted on a bio-disc comprising: (1) gold reflective base disc, treated with photo-lithography to remove the gold in specific capture zones, with appropriate chemistry placed over the capture zones, (2) 25 um thick channel layer, and (3) gold reflective cover disc, assembled into a functional bio-disk.

Whole blood is centrifuged at an appropriate speed and time to result in a pellet of cells and non-hemolyzed serum or plasma. The serum or plasma is separately mixed with Type $A_1$ and Type B Reagent Red Blood Cells (Ortho Clinical Diagnostics). The mixture of the cells and serum or plasma may take place in test tubes or directly on the disk in a mixing chamber. If the mixing occurs in a test tube, each mixture is then placed in separate channels of the disk. After a short, room temperature incubation (2 to 5 minutes) to allow the serum or plasma to interact with the reagent red blood cells, the disk is placed into the drive. The automated agglutination-detection software developed in-house centrifuges the disk, causing the agglutinated and/or non-agglutinated cells to travel over the capture zone and be non-specifically captured. Excess cells will be centrifuged to the outer edge of the flow channel. The disk is scanned with the standard 780 nm laser of the optical drive using the bottom detector and the software registers The program algorithm determines which reagent red blood cells were agglutinated and assigns an ABO phenotype, based on reverse typing to the plasma or serum sample. The entire process takes about 10 minutes from insertion of disk into the drive and receiving the reverse blood typing. The forward and reverse typings of an individual should be in agreement, signifying the correct typing of that individual.

Those skilled in the art will recognize, or be able to ascertain, using no more than routine experimentation, many equivalents to the specific embodiments of the invention described herein. Such equivalents are intended to be encompassed by the following claims.

What is claimed is:

1. An optical-bio disc for performing a blood-typing assay, said disc configured to be rotated and said disc comprising:
   a substrate;
   a separation chamber in proximity to said substrate, said separation chamber including a first portion and a second portion, wherein the first portion contains a filter means and includes a first inlet port positioned at an opening of said disc such that a material delivered from a non-disc source is deposited directly on said filter means;
   a first mixing chamber in direct fluid communication with said second portion of said separation chamber so as to receive material communicated directly from the separation chamber;
   a second inlet port connected to the first mixing chamber and configured to communicate material received from a source other than the separation chamber to the first mixing chamber;
   a second mixing chamber in direct fluid communication with said second portion of said separation chamber so as to receive material communicated directly from the separation chamber;

a third inlet port connected to the second mixing chamber and configured to communicate material received from a source other than the separation chamber to the second mixing chamber;

a first detection chamber in direct fluid communication with said first mixing chamber, said first detection chamber including a first capture field; and a second detection chamber in direct fluid communication with said second mixing chamber, said second detection chamber including a second capture field;

wherein the disc and chambers are configured such that fluid is transmitted from at least one of the chambers to another of the chambers that is in fluid communication therewith in response to rotation of the disc.

2. An optical-bio disc as defined in claim 1, wherein the separation chamber, the first and second mixing chambers and the first and second detection chambers are formed in the substrate.

3. An optical-bio disc as defined in claim 1, further comprising a cap that is bonded to the substrate.

4. An optical-bio disc as defined in claim 3, wherein the separation chamber, the first and second mixing chambers and the first and second detection chambers are formed in the cap.

5. An optical-bio disc as defined in claim 3 wherein the separation chamber, the first and second mixing chambers and the first and second detection chambers are partially formed in the cap and partially formed in the substrate such that the cap and substrate are bonded together in register to thereby fully form the chambers.

6. An optical-bio disc as defined in claim 3 further comprising a channel layer bonded between the cap and the substrate.

7. An optical-bio disc as defined in claim 6, wherein the separation chamber, the first and second mixing chamber and the first and second detection chambers are formed in the channel layer.

8. An optical-bio disc as defined in claim 1, further comprising an information layer which is configured to retain encoded information, said information layer located on the disc in a configuration such that the encoded information is readable by a disc drive.

9. An optical-bio disc as defined in claim 8, wherein the encoded information is used to define the manner in which the disc will be rotated.

10. An optical-bio disc as defined in claim 8, wherein the information layer is reflective.

11. An optical-bio disc as defined in claim 8, wherein the information layer is partially transmissive and partially reflective.

12. An optical-bio disc for performing a blood-typing assay, said disc configured to be rotated and said disc comprising:

a substrate;

a separation chamber having components that are at least partially supported by the substrate, said separation chamber including a first portion and a second portion, wherein the first portion contains a filter and includes a first inlet port positioned at an opening of said disc such that a material delivered from a non-disc source is deposited directly on said filter;

a plurality of mixing chambers, each of which is separate from the other mixing chambers and each of which is in direct fluid communication with said second portion of said separation chamber so as to receive material communicated directly from the separation chamber, and each of which includes an inlet port configured to communicate material into the mixing chamber from a source other than the separation chamber; and a plurality of detection chambers each of which is separate from the other detection chambers and each of which is in direct fluid communication with one of the mixing chambers;

wherein the disc and chambers are configured such that fluid is transmitted from at least one of the chambers to another of the chambers that is in fluid communication therewith in response to rotation of the disc.

13. An optical-bio disc as defined in claim 12, wherein the separation chamber, the plurality of mixing chambers and the plurality of detection chambers are formed in the substrate.

14. An optical-bio disc as defined in claim 12, wherein each of the plurality of detection chambers further comprises a capture zone.

15. An optical-bio disc as defined in claim 12, further comprising a cap that is bonded to the substrate.

16. An optical-bio disc as defined in claim 15, wherein the separation chamber, the plurality of mixing chambers and the plurality of detection chambers are formed in the cap.

17. An optical-bio disc as defined in claim 15, wherein the separation chamber, the plurality of mixing chambers and the plurality of detection chambers are partially formed in the cap and partially formed in the substrate, such that the cap and substrate are bonded together in register to thereby form the chambers.

18. An optical-bio disc as defined in claim 15 further comprising a channel layer bonded between the cap and the substrate.

19. An optical-bio disc as defined in claim 18, wherein the separation chamber, the plurality of mixing chambers and the plurality of detection chambers are formed in the channel layer.

* * * * *

UNITED STATES PATENT AND TRADEMARK OFFICE
CERTIFICATE OF CORRECTION

PATENT NO.        : 7,087,203 B2                          Page 1 of 2
APPLICATION NO.   : 09/988850
DATED             : August 8, 2006
INVENTOR(S)       : Gordon et al.

It is certified that error appears in the above-identified patent and that said Letters Patent is hereby corrected as shown below:

On the title page item (54) and Col. 1, line 2, delete "DISC" and insert -- DISCs --, therefor.

On the title page item (56), Col. 2 (Other Publications) Line 3 Delete "ultracentrifucation," and insert -- ultracentrifugation, --, therefor.

On the title page item (56), Col. 2 (Other Publications) Line 3 Delete "p.341-347." and insert -- pp. 341-347. --, therefor.

Sheet 23 of 24 FIG. 18 Delete "MICROFILLER(S)" and insert -- MICROFILTER(S) --, therefor.

Col. 1 Line 9 Delete "60/252,796," and insert -- 60/252,726, --, therefor.

Col. 5 Line 32 (Approx.) Delete "phenotyype;" and insert -- phenotype; --, therefor.

Col. 7 Line 22 After "In" delete "an" and insert -- a --, therefor.

Col. 8 Line 50 Delete "agen." and insert -- agent. --, therefor.

Col. 8 Line 51 Delete "annd" and insert -- and --, therefor.

Col. 9 Line 17 Delete "FIG." and insert -- FIGS. --, therefor.

Col. 14 Line 50-After "etc.)" insert -- . --.

Col. 15 Line 16 (Table 1 )-12 Delete "inmmunoglobulin," and insert -- immunoglobulin, --, therefor.

Col. 16 Line 27-Delete "showts" and insert -- shows --, therefor.

Col. 16 Line 29-Delete "steptavidin" and insert -- streptavidin --, therefor.

Col. 19 Line 23-Delete "FIGS." and insert -- FIG. --, therefor.

Col. 19 Line 46-Delete "(FIG." and insert -- (FIGS. --, therefor.

Col. 21 Line 10-Delete "thereto," and insert -- thereto. --, therefor.

Col. 21 Line 54 Delete "(FIG." and insert (FIGS. --, therefor.

UNITED STATES PATENT AND TRADEMARK OFFICE
CERTIFICATE OF CORRECTION

PATENT NO. : 7,087,203 B2
APPLICATION NO. : 09/988850
DATED : August 8, 2006
INVENTOR(S) : Gordon et al.

It is certified that error appears in the above-identified patent and that said Letters Patent is hereby corrected as shown below:

Col. 24 Line 5 Delete "agen." and insert -- agent. --, therefor.

Col. 24 Line 6 Delete "annd" and insert -- and --, therefor.

Col. 24 Line 38 (Approx.) After "in" delete "a" and insert -- an --, therefor.

Col. 24 Line 54 Delete "MgCl2)" and insert -- $MgCl_2$) --, therefor.

Col. 25 Line 2 Delete "MgCl2)" and insert -- $MgCl_2$) --, therefor.

Col. 25 Line 20 Delete "MgCl2)" and insert -- $MgCl_2$) --, therefor.

Col. 26 Line 30 After "registers" insert -- . --.

Signed and Sealed this

Eighth Day of May, 2007

JON W. DUDAS
*Director of the United States Patent and Trademark Office*